United States Patent
Takeuchi

(10) Patent No.: US 12,042,618 B2
(45) Date of Patent: Jul. 23, 2024

(54) CONNECTOR

(71) Applicant: JMS CO., LTD., Hiroshima (JP)

(72) Inventor: Masahiko Takeuchi, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 638 days.

(21) Appl. No.: 17/279,415

(22) PCT Filed: Sep. 20, 2019

(86) PCT No.: PCT/JP2019/037088
§ 371 (c)(1),
(2) Date: Mar. 24, 2021

(87) PCT Pub. No.: WO2020/066938
PCT Pub. Date: Apr. 2, 2020

(65) Prior Publication Data
US 2022/0008708 A1  Jan. 13, 2022

(30) Foreign Application Priority Data

Sep. 27, 2018 (JP) ................................ 2018-182210

(51) Int. Cl.
*A61M 39/10* (2006.01)
(52) U.S. Cl.
CPC ..... *A61M 39/10* (2013.01); *A61M 2039/1077* (2013.01); *A61M 2205/02* (2013.01)
(58) Field of Classification Search
CPC .......... A61M 39/10; A61M 2039/1077; A61M 2205/02
See application file for complete search history.

(56) References Cited

U.S. PATENT DOCUMENTS 6,468,251 B1  10/2002  Yamanaka et al.
2005/0245899 A1*  11/2005  Swisher .............. A61M 39/223
604/533

(Continued)

FOREIGN PATENT DOCUMENTS

CN  104755130  7/2015
EP  2 712 652  4/2014

(Continued)

OTHER PUBLICATIONS

Office Action issued in corresponding Chinese Patent Application No. 201980061879.1, Apr. 20, 2022, 17 pages w/translation.

(Continued)

*Primary Examiner* — Nathan R Price
*Assistant Examiner* — Mark A Igel
(74) *Attorney, Agent, or Firm* — HSML P.C.

(57) ABSTRACT

A first member (10) and a second member (20) are coupled to each other in a coupling portion (100). The first member includes, on the opposite side to the coupling portion, a main portion (51) that is connectable to a counterpart connector. The main portion and the second member are in communication with each other via a flow channel (102). One of the first member and the second member includes an outer cylindrical portion (30), and the other of the first member and the second member includes an inner cylindrical portion (40). In the coupling portion, the inner cylindrical portion is fitted in the outer cylindrical portion. The outer cylindrical portion includes a first engagement portion (31) and an abutment portion (35). The inner cylindrical portion includes a second engagement portion (41) that engages the first engagement portion, and a leading end (45) that is a front end of the inner cylindrical portion in a direction in which the inner cylindrical portion is fitted into the outer cylindrical portion. As a result of the first engagement (Continued)

portion and the second engagement portion engaging each other, the leading end of the inner cylindrical portion abuts against the abutment portion of the outer cylindrical portion along a central axis (101).

14 Claims, 12 Drawing Sheets

(56) References Cited

U.S. PATENT DOCUMENTS

| | | | |
|---|---|---|---|
| 2011/0160679 | A1 | 6/2011 | Okiyama et al. |
| 2012/0041425 | A1 | 2/2012 | Tsunematsu et al. |
| 2014/0228815 | A1 | 8/2014 | Haag et al. |
| 2015/0258324 | A1 | 9/2015 | Chida et al. |
| 2016/0206516 | A1 | 7/2016 | Kunishige et al. |
| 2018/0008813 | A1* | 1/2018 | Ueda .................. A61M 39/10 |

FOREIGN PATENT DOCUMENTS

| | | |
|---|---|---|
| JP | 52-83294 U | 6/1977 |
| JP | 11-197254 | 7/1999 |
| JP | 2007-532274 | 11/2007 |
| JP | 2008-029607 | 2/2008 |
| JP | 2010-075684 | 4/2010 |
| JP | 2013-135729 | 7/2013 |
| JP | 2013-252165 | 12/2013 |
| JP | 2017-148444 | 8/2017 |
| JP | 2017148444 A * | 8/2017 |
| WO | 2005/102436 | 11/2005 |
| WO | 2010/122988 | 10/2010 |
| WO | 2015/034045 | 3/2015 |
| WO | 2016/152137 | 9/2016 |

OTHER PUBLICATIONS

International Search Report issued in International Application No. PCT/JP2019/037088, Nov. 19, 2019, 4 pages w/translation.
Extended European Search Report issued in corresponding European Patent Application No. 19867373.3, Jun. 1, 2022, 9 pages.
1st Written Opinion issued is corresponding Singapore Patent Application No. 11202102745T, Nov. 8, 2022, 11 pages.

* cited by examiner

CONNECTOR

TECHNICAL FIELD

The present invention relates to a connector that can be favorably used for medical applications.

BACKGROUND ART

In the field of medicine, flow channels (also called "circuits") through which various types of liquids, such as drug solutions and blood, flow are formed using flexible tubes. In order to connect different tubes, a connecting device is used. In general, the connecting device is constituted by a male connector and a female connector that can be repeatedly connected to and disconnected from each other.

For example, each of the male connector and the female connector is connected to an end of a tube (see Patent Document 1, for example). In general, a connector (the term "connector" as used in the present invention includes both a male connector and a female connector) is made of a hard resin material that substantially does not deform when subjected to an external force. As a method for connecting the hard connector to a flexible tube, adhesion using a solvent or thermal fusing is often used. However, with these methods, depending on the combination of the materials of the connector and the tube, there are cases where it is difficult to connect the connector to the tube while achieving desired strength and sealability.

Patent Document 2 discloses a connector formed by integrating, using a two-color injection molding method, a first member unit having a male luer that is connectable to a female connector with a second member unit to which a tube can be connected. A connector that has good connectivity to a tube can be obtained by selecting, as the material of the second member unit, a material that is different from the material of the first member unit with consideration given to the connectivity to a tube.

PRIOR ART DOCUMENTS

Patent Documents
  [Patent Document 1] JP 2013-135729A
  [Patent Document 2] WO 2010/122988
  [Patent Document 3] JP 2008-029607A
  [Patent Document 4] JP H11-197254A
  [Patent Document 5] JP 2010-075684A
  [Patent Document 6] JP 2013-252165A

DISCLOSURE OF INVENTION

Problem to be Solved by the Invention

However, the production of the connector disclosed in Patent Document 2 is complicated because the first member unit and the second member unit, which are made of different materials, need to be integrated with each other using a two-color injection molding method.

Furthermore, the connectors disclosed in Patent Documents 1 and 2 have an issue in which, for example, when a tube that has a different diameter is to be connected, a connector suited to that tube needs to be newly designed and produced. Also, when the connector is to be provided integrally with an additional member (e.g., a bypass injection port) other than the tube to thereby form a single unit, an entire unit including the connector and the additional member needs to be newly designed and produced. Thus, multiple types of connectors that are largely similar with one another but are only partially different from one another are needed, and this makes management of connectors more complicated and increases the cost of connectors. Therefore, there is demand for a highly versatile connector with a configuration that enables replacement of only a portion that has been subjected to a design change.

An object of the present invention is to provide a connector that can be easily produced and is highly versatile.

Means for Solving Problem

A connector of the present invention includes a first member and a second member. The first member and the second member are coupled to each other in a coupling portion. The first member includes, on a side opposite to the coupling portion, a main portion that can be connected to and disconnected from a counterpart connector other than the connector. A flow channel via which the main portion and the second member are in communication with each other extends along a central axis of the connector. One of the first member and the second member includes an outer cylindrical portion that has a hollow cylindrical shape and is coaxial with the central axis. The other of the first member and the second member includes an inner cylindrical portion that has a hollow cylindrical shape and is coaxial with the central axis. In the coupling portion, the inner cylindrical portion is fitted in the outer cylindrical portion. The outer cylindrical portion includes a first engagement portion and an abutment portion. The inner cylindrical portion includes a second engagement portion that engages the first engagement portion, and a leading end that is a front end of the inner cylindrical portion in a direction in which the inner cylindrical portion is fitted into the outer cylindrical portion. As a result of the first engagement portion and the second engagement portion engaging each other, the leading end of the inner cylindrical portion abuts against the abutment portion of the outer cylindrical portion along the central axis.

Effects of the Invention

The connector of the present invention is obtained by producing the first member and the second member separately and then coupling the first member and the second member together to form a single unit. Therefore, the connector can be easily produced.

It is possible to obtain multiple types of connectors by replacing the first member or the second member. Therefore, the connector of the present invention is highly versatile.

Since the leading end of the inner cylindrical portion abuts against the abutment portion of the outer cylindrical portion along the central axis, an inner circumferential surface of the flow channel is continuous without a gap between the leading end of the inner cylindrical portion and the abutment portion of the outer cylindrical portion.

DESCRIPTION OF THE INVENTION

Figure 1:
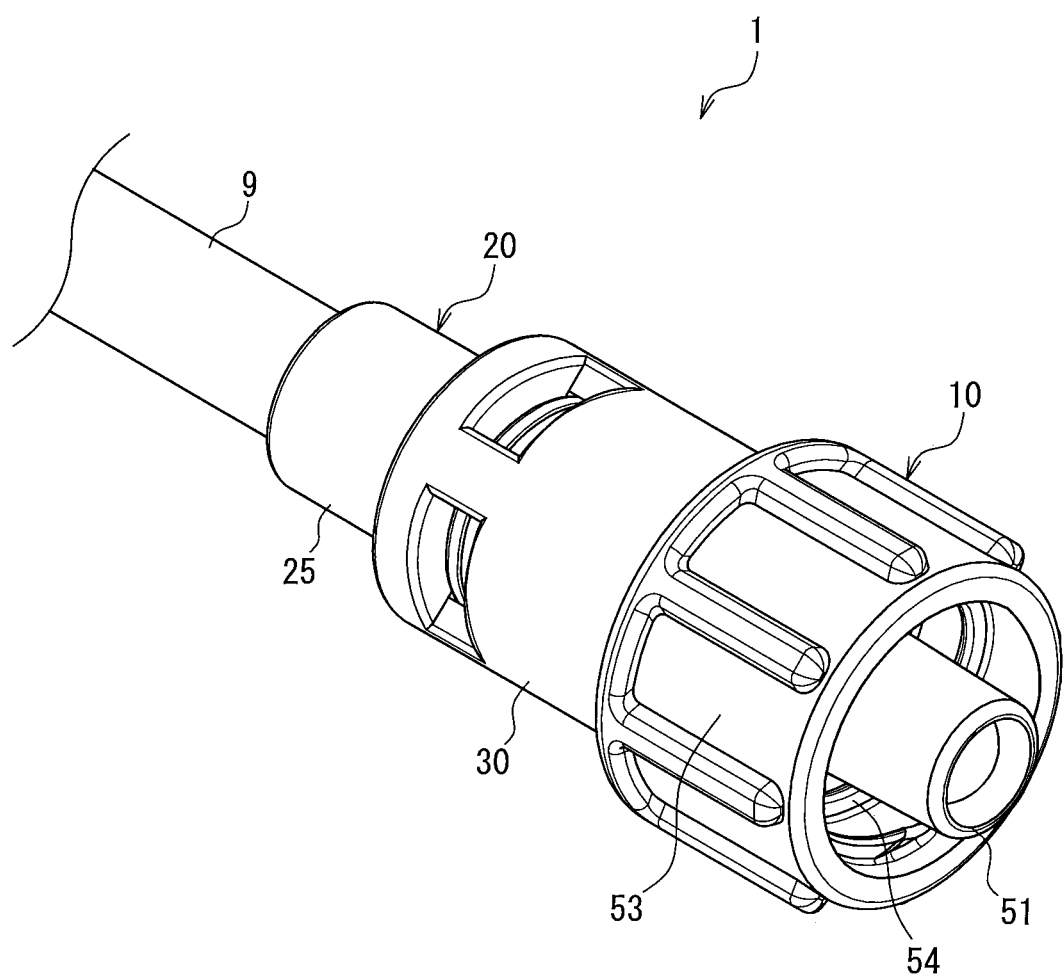
FIG. 1 is a perspective view of a connector according to Embodiment 1 of the present invention.

In the above-described connector of the present invention, at least one of the first engagement portion and the second engagement portion may have an inclined surface that is inclined relative to the central axis. The inclined surface may be inclined such that the leading end of the inner cylindrical portion abuts against the abutment portion of the outer cylindrical portion along the central axis. This configuration is advantageous in realizing abutment of the leading end of the inner cylindrical portion against the abutment portion of the outer cylindrical portion using a simple configuration.

The leading end of the inner cylindrical portion may annularly abut against the abutment portion so as to surround the flow channel. This configuration is advantageous in obtaining an inner circumferential surface of the flow channel of the connector that is continuous without a gap between the first member and the second member.

An inner circumferential surface of the outer cylindrical portion may have a first fitting surface. An outer circumferential surface of the inner cylindrical portion may have a second fitting surface that is fitted to the first fitting surface. This configuration is advantageous in obtaining an inner circumferential surface of the flow channel of the connector that is continuous without a level difference between the first member and the second member.

As a result of the first fitting surface and the second fitting surface being fitted to each other, the outer cylindrical portion and the inner cylindrical portion may be coaxially positioned. This configuration is even more advantageous in obtaining an inner circumferential surface of the flow channel of the connector that is continuous without a level difference between the first member and the second member.

A liquid-tight seal may be formed between the first fitting surface and the second fitting surface. This configuration is advantageous, firstly, in preventing a liquid that flows through the flow channel from leaking out of the connector through a gap between the first member and the second member, and secondly, in forming a liquid-tight seal using a simple configuration.

A lubricant may be added between the first fitting surface and the second fitting surface. The lubricant is advantageous, firstly, in forming a liquid-tight seal between the first fitting surface and the second fitting surface, and secondly, in making the first member rotatable relative to the second member.

An inner circumferential surface of the flow channel may be continuous without a level difference and a gap between the first member and the second member. This configuration is advantageous in preventing a stagnation portion in which the liquid flowing through the flow channel stagnates from being formed in the flow channel.

The first member may be rotatable relative to the second member. In the case where, for example, a tube is connected to the second member, this configuration makes it possible to sever a link between rotation of the first member and twisting of the tube. Also, in the case where the second member is provided on a bypass injection port, this configuration makes it easy to rotate the bypass injection port so that the bypass injection port is oriented in any suitable direction.

The first member may be unrotatable relative to the second member. In the case where, for example, the first member is provided with a screw lock mechanism for maintaining a state in which the connector is connected to the counterpart connector, this configuration makes it easy to perform a screwing operation and an unscrewing operation.

The main portion may include a male member or a female member. In the case where the main portion includes a male member, the connector of the present invention can function as a male connector, and in the case where the main portion includes a female member, the connector of the present invention can function as a female connector.

The second member may be connectable to an end of a flexible tube. This configuration makes it possible to connect the tube to another member via the connector of the present invention.

The second member may be provided on a bypass injection port. This configuration makes it possible to connect the bypass injection port to another member via the connector of the present invention.

The first member and the second member may be made of different materials. With this configuration, an optimal material can be selected for each of the materials of the first member and the second member. For example, in the case where the second member is to be connected to a tube, the material of the second member can be selected with consideration given to the connectivity to the tube.

Hereinafter, the present invention will be described in detail while showing preferred embodiments thereof. However, it goes without saying that the present invention is not limited to the embodiments below. In the drawings that will be referred to in the following description, only the main members of constituent members of the embodiments of the present invention are shown in a simplified manner for the sake of convenience of description. Therefore, an optional member that is not shown in the drawings may be added, or any of the members shown in the drawings may be changed or omitted, without departing from the scope of the present invention. In the drawings that will be referred to in the description of the embodiments below, members corresponding to those members shown in the drawings that are referred to in the description of any preceding embodiment are denoted by the same reference numerals as, or by reference numerals corresponding to, the reference numerals of the members shown in the drawings of that preceding embodiment. With respect to such members, redundant descriptions are omitted, and the description of the preceding embodiment should be taken into account.

Embodiment 1

Figure 2:
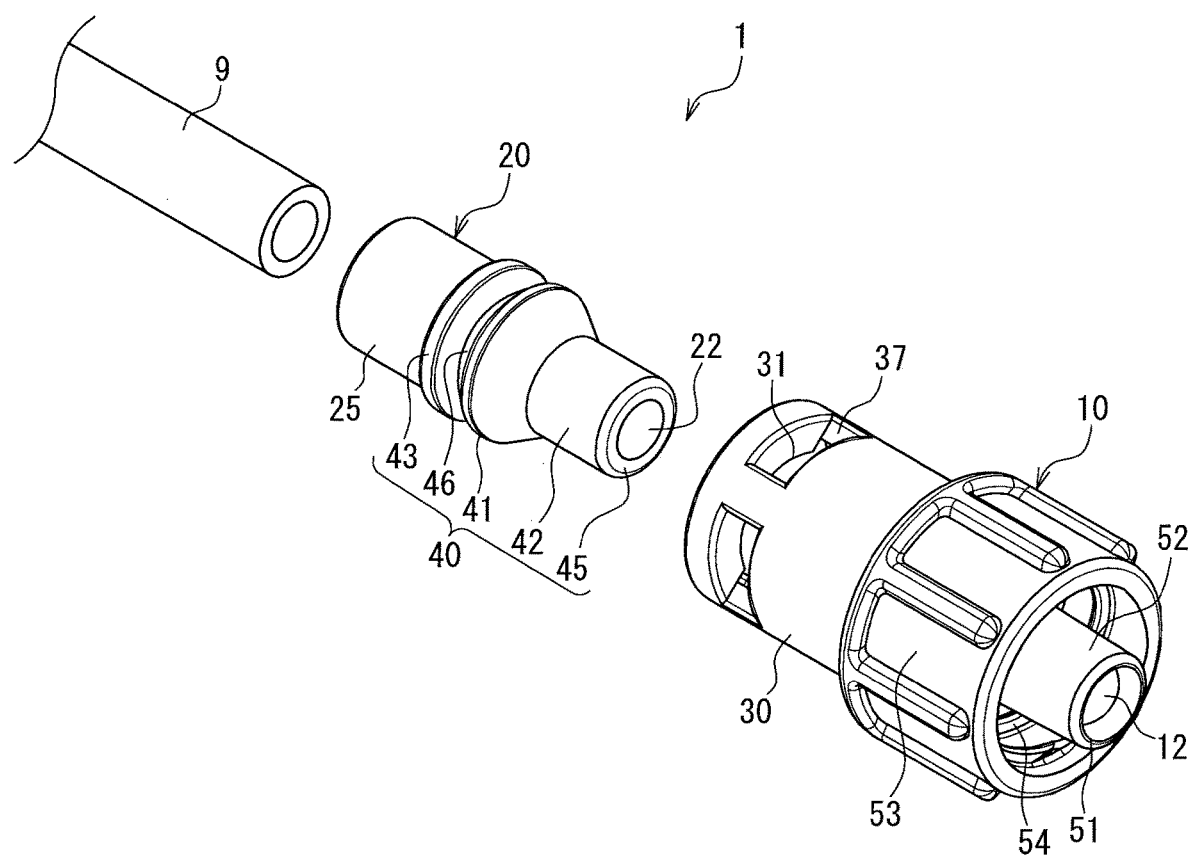
FIG. 2 is an exploded perspective view of the connector according to Embodiment 1 of the present invention.

FIG. 1 is a perspective view of a connector 1 according to Embodiment 1 of the present invention. FIG. 2 is an exploded perspective view of the connector 1. The connector 1 is a male connector that has a male member (male luer) 51. The connector 1 is provided at an end of a flexible tube 9. The connector 1 includes a first member 10 that has the male member 51, and a second member 20 that is provided on the tube 9. The first member 10 and the second member 20 are coupled to each other as a result of the second member 20 being inserted into the first member 10. The first member 10 and the tube 9 are connected to each other via the second member 20. For the sake of convenience of the following description, relative to the tube 9, a side that is close to the tube 9 will be referred to as a "proximal" side, and a side that is far from the tube 9 will be referred to as a "distal" side. A direction of rotation about the central axis will be referred to as a "circumferential direction".

Figure 3A:
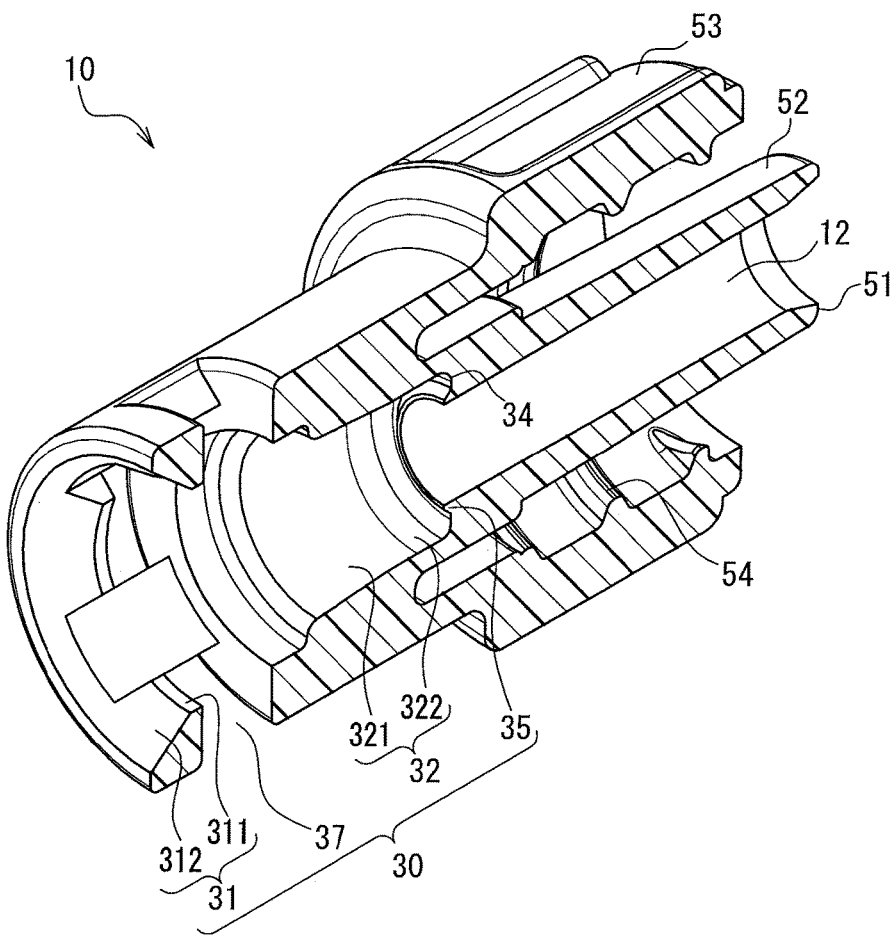
FIG. 3A is a cross-sectional perspective view of a first member according to Embodiment 1 of the present invention.
Figure 3B:
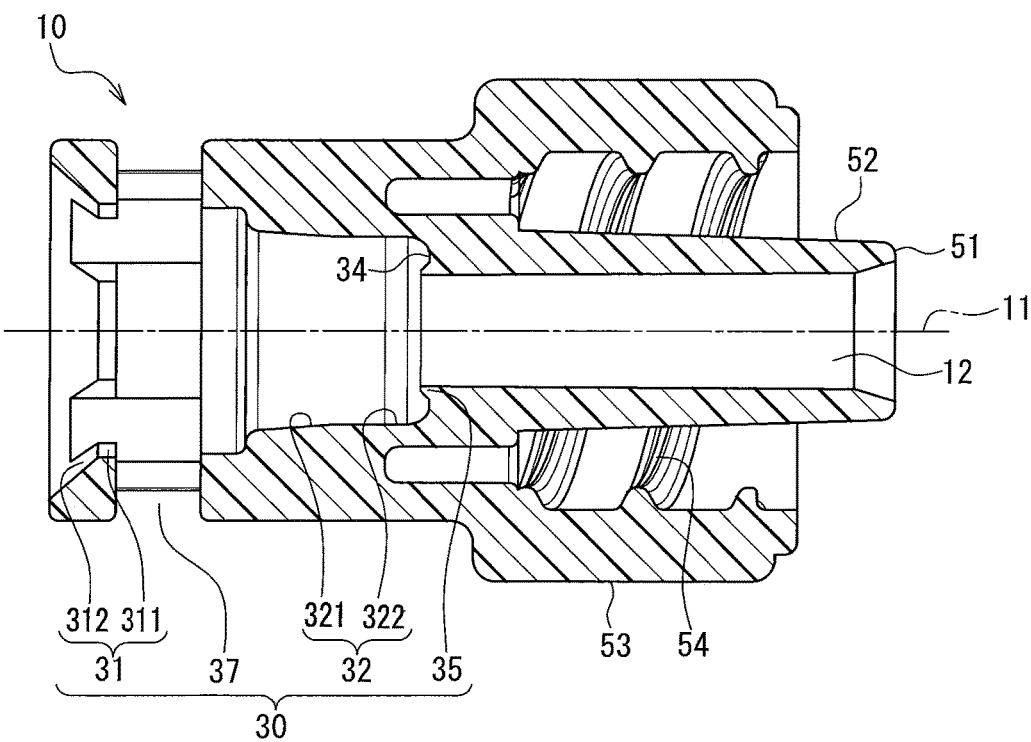
FIG. 3B is a cross-sectional view of the first member according to Embodiment 1 of the present invention.

FIG. 3A is a cross-sectional perspective view of the first member 10 when viewed from the proximal side, and FIG. 3B is a cross-sectional view of the first member 10. Both of the cross sections shown in FIGS. 3A and 3B contain a central axis 11 of the first member 10. The first member 10 has a hollow, substantially circular cylindrical shape as a whole that is coaxial with the central axis 11. The first member 10 includes, on its distal side, the male member 51 that can be connected to an additional connector (counterpart connector) other than the connector 1, and also includes, on its proximal side (the opposite side to the male member 51), an outer cylindrical portion 30 into which an inner cylindrical portion 40 (see FIG. 2) of the second member 20 can be inserted. A flow channel 12 passes through the male member 51 along the central axis 11.

The outer cylindrical portion 30 has a hollow, substantially circular cylindrical shape that is coaxial with the central axis 11. An inner circumferential surface of the outer cylindrical portion 30 has four first engagement portions 31, a first fitting surface 32, and an annular rib 35 that are sequentially provided in this order from an open end (proximal side) of the outer cylindrical portion 30 toward the male member 51 (distal side). Also, the outer cylindrical portion 30 has four lateral holes 37 that are located at positions between the first fitting surface 32 and the first engagement portions 31 and penetrate the outer cylindrical portion 30 in a radial direction. The first engagement portions 31 are provided along opening end edges of the respective lateral holes 37 on the proximal side.

The first engagement portions 31 are protrusions (or claws) that protrude inward in the radial direction from the inner circumferential surface of the outer cylindrical portion 30. The first engagement portions 31 each have a crest portion 311 that protrudes the farthest inward in the radial direction and an inclined surface 312 that extends from the crest portion 311 toward the proximal side. The inclined surfaces 312 are tapered surfaces (conical surfaces) that are inclined such that the inner diameter of the outer cylindrical portion 30 gradually increases toward the proximal side. The four first engagement portions 31 are arranged at regular intervals in the circumferential direction.

The first fitting surface 32 is constituted by a tapered surface 321 and a circular cylindrical surface 322 that is located on the distal side of the tapered surface 321 and is adjacent thereto. The tapered surface 321 and the circular cylindrical surface 322 are both coaxial with the central axis 11. The tapered surface 321 is a tapered surface (conical surface) whose inner diameter gradually increases toward the proximal side. The circular cylindrical surface 322 has an inner diameter that is equal to the inner diameter of the tapered surface 321 at a distal end thereof. The maximum inner diameter of the first fitting surface 32 (i.e., the inner diameter of the tapered surface 321 at a proximal end thereof) is smaller than the diameter of an inscribed circle of the crest portions 311 of the first engagement portions 31. Although the first fitting surface 32 of the present embodiment is constituted by the tapered surface 321 and the circular cylindrical surface 322, either the tapered surface 321 or the circular cylindrical surface 322 may be omitted. The first fitting surface 32 may also include an additional surface other than the tapered surface 321 and the circular cylindrical surface 322. However, it is preferable that the additional surface is a circular cylindrical surface, or a tapered surface whose diameter gradually increases toward the proximal side.

The inner diameter of the first fitting surface 32 is larger than the inner diameter of the flow channel 12 (i.e., the inner diameter of the male member 51). Accordingly, there is a step surface 34 between the first fitting surface 32 and an inner circumferential surface of the flow channel 12, the step surface 34 being formed due to the difference in inner diameter between the first fitting surface 32 and the inner circumferential surface of the flow channel 12. The step surface 34 is a ring-shaped flat surface and extends along a plane perpendicular to the central axis 11. The annular rib 35 having a substantially circular cylindrical shape protrudes from the step surface 34 toward the proximal side. The annular rib 35 is arranged along an end edge of the step surface 34 on the inner circumferential side in such a manner that the inner circumferential surface of the flow channel 12 is extended toward the proximal side beyond the step surface 34. The annular rib 35 is spaced apart from the first fitting surface 32 inward in the radial direction.

The male member 51 has a hollow, cylindrical shape that is coaxial with the central axis 11 and through which the flow channel 12 passes. An outer circumferential surface 52 of the male member 51 is a tapered surface (a so-called male tapered surface) whose outer diameter gradually decreases toward a leading end (distal end) of the male member 51. A lock cylinder 53 having a circular cylindrical shape is provided spaced apart from the male member 51 in the radial direction and surrounds the male member 51. A female thread 54 is formed on an inner circumferential surface of the lock cylinder 53 that opposes the male member 51. The male member 51 and the female thread 54 together constitute a so-called screw-lock type male connector (see Patent Document 1, for example).

The flow channel 12 extends from the annular rib 35 to the leading end of the male member 51 along the central axis 11. The flow channel 12 has a circular shape in cross section along a plane perpendicular to the central axis 11 at any position in the direction of the central axis 11. In the present embodiment, the inner diameter of the flow channel 12 is constant in the direction of the central axis 11. However, the present invention is not limited to this. The inner diameter of the flow channel 12 may be varied along the central axis 11.

For example, the inner diameter of the flow channel 12 may gradually increase toward the proximal side or the distal side.

Figure 4A:
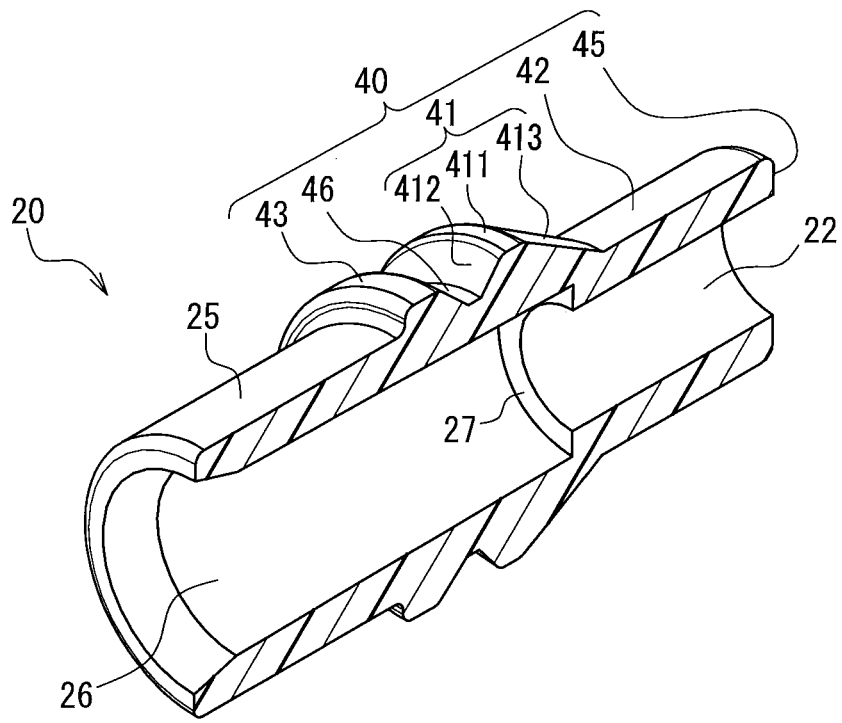
FIG. 4A is a cross-sectional perspective view of a second member according to Embodiment 1 of the present invention.
Figure 4B:
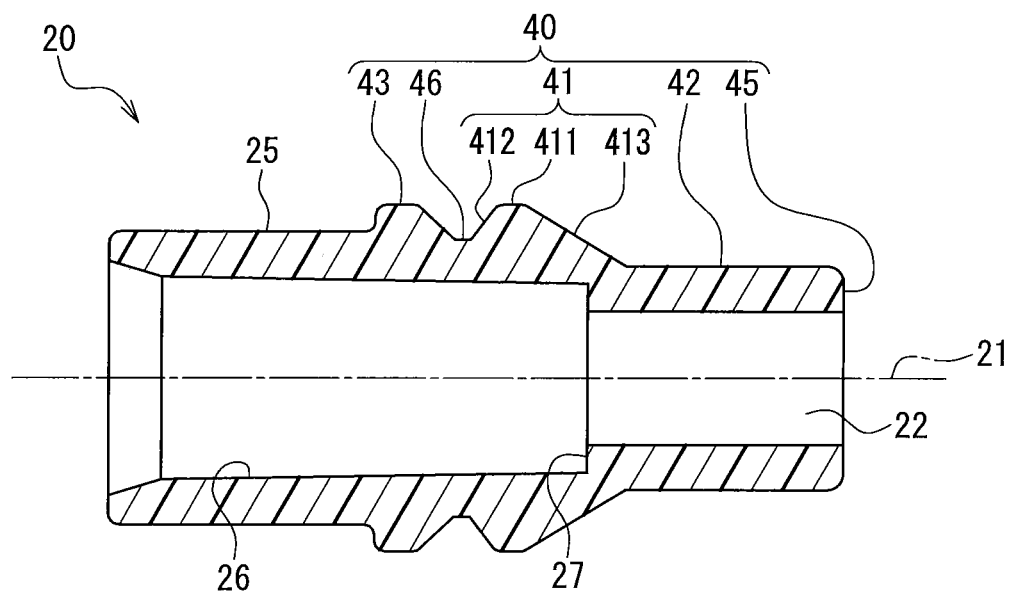
FIG. 4B is a cross-sectional view of the second member according to Embodiment 1 of the present invention.

FIG. 4A is a cross-sectional perspective view of the second member 20 when viewed from the proximal side, and FIG. 4B is a cross-sectional view of the second member 20. The cross sections shown in FIGS. 4A and 4B contain a central axis 21 of the second member 20. The second member 20 has a hollow, substantially circular cylindrical shape as a whole that is coaxial with the central axis 21. The second member 20 includes, on its distal side, the inner cylindrical portion 40 that can be inserted into the outer cylindrical portion 30 of the first member 10, and also includes, on its proximal side, a base portion 25 to which the tube 9 (see FIG. 2) can be connected.

The inner cylindrical portion 40 has a hollow, substantially circular cylindrical shape that is coaxial with the central axis 21. A flow channel 22 extending along the central axis 21 passes through the inner cylindrical portion 40. A leading end 45 of the inner cylindrical portion 40 extends in a ring shape along a plane perpendicular to the central axis 21 of the second member 20. Note that the term "leading end" of the inner cylindrical portion 40 as used in the present invention means the front end of the inner cylindrical portion 40 when the inner cylindrical portion 40 is inserted into the outer cylindrical portion 30 (see FIG. 2). In Embodiment 1, a distal end of the inner cylindrical portion 40 corresponds to the leading end 45. An outer circumferential surface of the inner cylindrical portion 40 has a second fitting surface 42, a second engagement portion 41, and a protrusion 43 that are sequentially provided in this order from the leading end 45 toward the base portion 25.

The second fitting surface 42 includes a tapered surface (conical surface) whose outer diameter gradually decreases toward the leading end 45, or a circular cylindrical surface. In Embodiment 1, the second fitting surface 42 is a tapered surface having a taper angle that is smaller than the taper angle of the tapered surface 321 (see FIGS. 3A and 3B) of the first fitting surface 32 of the outer cylindrical portion 30. The second fitting surface 42 is designed so as to fit to the first fitting surface 32 when the inner cylindrical portion 40 is inserted into the outer cylindrical portion 30.

The second engagement portion 41 is a protrusion (or a rib) that protrudes outward in the radial direction from the outer circumferential surface of the inner cylindrical portion 40. The second engagement portion 41 is continuous in the circumferential direction and has an annular shape. The second engagement portion 41 includes a crest portion 411 that protrudes the farthest outward in the radial direction, a first inclined surface 412 that extends from the crest portion 411 toward the proximal side (base portion 25 side), and a second inclined surface 413 that extends from the crest portion 411 toward the distal side (leading end 45 side). The first inclined surface 412 is a tapered surface (or a conical surface) that is inclined such that the outer diameter of the inner cylindrical portion 40 gradually decreases toward the proximal side. The second inclined surface 413 is a tapered surface (or a conical surface) that is inclined such that the outer diameter of the inner cylindrical portion 40 gradually decreases toward the distal side. The inclination of the first inclined surface 412 relative to the central axis 21 is steeper than that of the second inclined surface 413.

The protrusion 43 protrudes outward in the radial direction from the outer circumferential surface of the inner cylindrical portion 40. The protrusion 43 is an annular rib that is continuous in the circumferential direction and has an annular shape. A recess 46 is formed between the second engagement portion 41 and the protrusion 43. The recess 46 is an annular groove and is continuous in the circumferential direction.

The base portion 25 has an inner circumferential surface 26 with an inner diameter that is approximately equal to the outer diameter of the tube 9 so that the tube 9 can be fitted into the base portion 25. The inner circumferential surface 26 is a circular cylindrical surface with an inner diameter that is larger than the inner diameter of the flow channel 22. There is a step surface 27 between the inner circumferential surface 26 and an inner circumferential surface of the inner cylindrical portion 40, the step surface 27 being formed due to the difference in inner diameter between the inner circumferential surface 26 and the inner circumferential surface of the inner cylindrical portion 40.

The flow channel 22 extends from the step surface 27 to the leading end 45 along the central axis 21 of the second member 20. The flow channel 22 has a circular shape in cross section along a plane perpendicular to the central axis 21 at any position in the direction of the central axis 21. The inner diameter of the flow channel 22 at its proximal end (i.e., an opening end edge of the step surface 27) is set to be equal to the inner diameter of the tube 9. The inner diameter of the flow channel 22 at its distal end (i.e., the leading end 45) is set to be equal to the inner diameter of the flow channel 12 of the first member 10 at its proximal end (i.e., the annular rib 35, see FIGS. 3A and 3B). The inner circumferential surface of the flow channel 22 is constituted by a tapered surface, a circular cylindrical surface, or a combination thereof so that the inner diameter of the flow channel 22 smoothly changes from the proximal end to the distal end thereof.

Figure 5A:
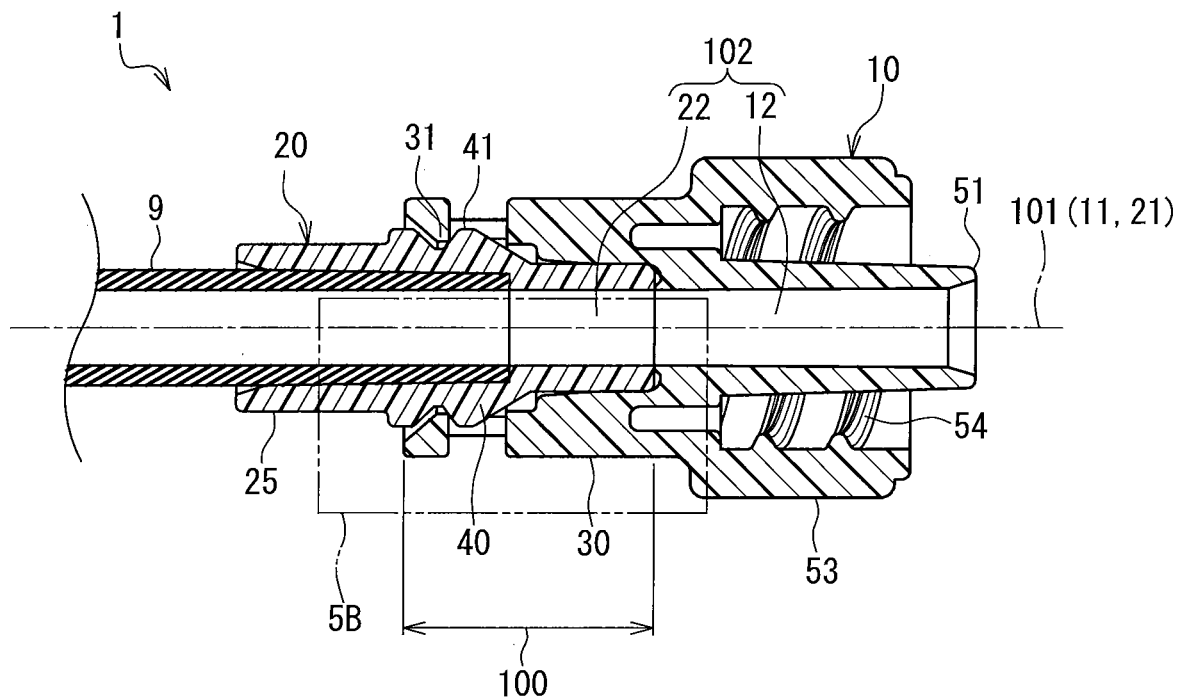
FIG. 5A is a cross-sectional view of the connector according to Embodiment 1 of the present invention.
Figure 5B:
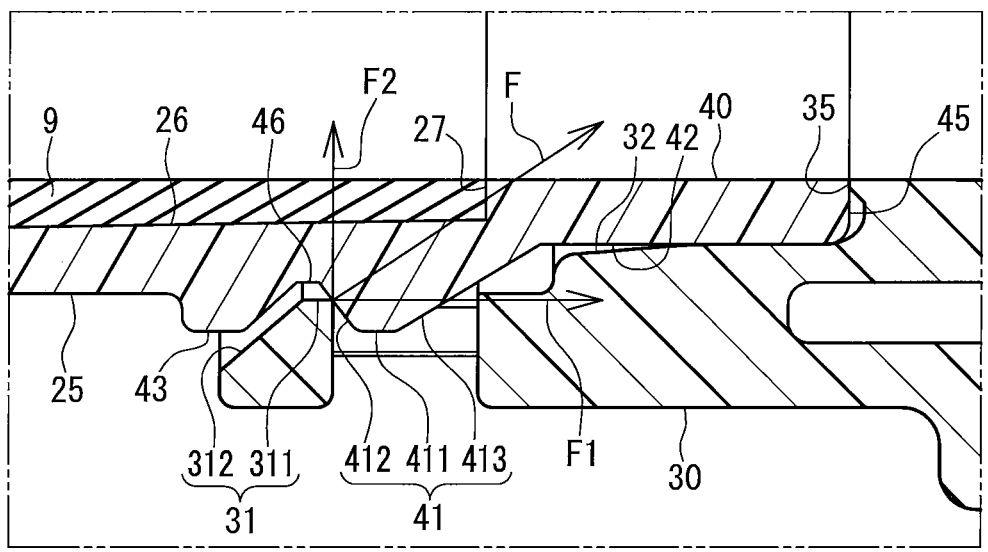
FIG. 5B is an enlarged cross-sectional view of a portion 5B in FIG. 5A.

FIG. 5A is a cross-sectional view of the connector 1. FIG. 5B is an enlarged cross-sectional view of a portion 5B in FIG. 5A. The inner cylindrical portion 40 of the second member 20 is inserted in the outer cylindrical portion 30 of the first member 10. A portion in which the outer cylindrical portion 30 and the inner cylindrical portion 40 together constitute a double-tube structure will be referred to as a coupling portion 100. In the coupling portion 100, the first member 10 and the second member 20 are coupled to each other. The flow channel 12 of the first member 10 and the flow channel 22 of the second member 20 are in communication with each other, thereby forming a flow channel 102 of the connector 1. The flow channel 102 extends along a central axis 101 of the connector 1. The central axis 101 coincides with the central axis 11 of the first member 10 and the central axis 21 of the second member 20. The tube 9 is inserted into and connected to the base portion 25 of the second member 20 and is coaxial with the central axis 101. The tube 9 is in communication with the flow channel 102. The tube 9 is in communication with the male member 51 via the flow channel 102.

As can be understood from FIGS. 5A and 5B, the coupling between the first member 10 and the second member 20 is achieved by producing the first member 10 and the second member 20 separately and then inserting and pushing the inner cylindrical portion 40 of the second member 20 into the outer cylindrical portion 30 of the first member 10 (see FIG. 2). The inclined surfaces 312 of the first engagement portions 31 of the outer cylindrical portion 30 guide the inner cylindrical portion 40 into the outer cylindrical portion 30.

The first engagement portions 31 of the outer cylindrical portion 30 move over the second engagement portion 41 of the inner cylindrical portion 40 and engage the second engagement portion 41. The inclined surfaces 312 of the first engagement portions 31 and the second inclined surface 413 of the second engagement portion 41 facilitate the movement of the first engagement portions 31 over the second engagement portion 41. Since the inclination of the first inclined surface 412 is steeper than that of the second inclined surface 413, once the first engagement portions 31 engage the second engagement portion 41 as shown in FIGS. 5A and 5B, it is difficult to release the engagement. That is to say, the first member 10 and the second member 20 are irreversibly coupled to each other.

The first engagement portions 31 are located in the recess 46 between the second engagement portion 41 and the protrusion 43. The protrusion 43 makes it difficult to access the crest portions 311 of the first engagement portions 31 from the proximal side. This is advantageous in preventing the connector 1 from being disassembled.

When the first engagement portions 31 have engaged the second engagement portion 41, the first engagement portions 31 (in particular, their crest portions 311) abut against the first inclined surface 412 of the second engagement portion 41. The first engagement portions 31 apply a pushing force F to the first inclined surface 412, the pushing force F acting in a direction perpendicular to the first inclined surface 412. The pushing force F can be broken up into the following components: an axial direction component F1 that acts parallel to the central axis 101 toward the leading end 45 of the inner cylindrical portion 40; and a radial direction component F2 that acts inward in the radial direction. The axial direction component F1 presses the leading end 45 of the inner cylindrical portion 40 against the annular rib 35 of the outer cylindrical portion 30 along the central axis 101. The leading end 45 is in areal contact with the annular rib 35 without a gap therebetween. In the vicinity of the boundary between the annular rib 35 and the leading end 45, the inner circumferential surface of the flow channel 12 of the first member 10 and the inner circumferential surface of the flow channel 22 of the second member 20 are continuous with each other in the direction of the central axis 101 without a gap therebetween. The engagement between the first engagement portions 31 and the second engagement portion 41 as well as the abutment between the leading end 45 and the annular rib 35 accommodate minute dimensional errors (production errors) in the outer cylindrical portion 30 and the inner cylindrical portion 40, and the inner cylindrical portion 40 is thus positioned relative to the outer cylindrical portion 30 without looseness in the direction of the central axis 101.

The second fitting surface 42 of the inner cylindrical portion 40 is fitted to the first fitting surface 32 of the outer cylindrical portion 30. The first and the second fitting surfaces 32 and 42 are arranged coaxially with the central axis 101 so as to annularly surround the flow channel 102. As a result of the second fitting surface 42 being fitted to the first fitting surface 32, the inner cylindrical portion 40 is coaxially aligned with the outer cylindrical portion 30 without eccentricity. Thus, misalignment of the leading end 45 of the inner cylindrical portion 40 relative to the annular rib 35 of the outer cylindrical portion 30 in the radial direction is reduced. In the vicinity of the boundary between the annular rib 35 and the leading end 45, the inner circumferential surface of the flow channel 12 of the first member 10 and the inner circumferential surface of the flow channel 22 of the second member 20 are smoothly continuous with each other without misalignment (or a level difference) in the radial direction.

The tube 9 is inserted into the base portion 25 of the second member 20 until the leading end of the tube 9 abuts against the step surface 27 of the second member 20. The step surface 27 limits the insertion depth of the tube 9 into the base portion 25. The inner circumferential surface 26 of the base portion 25 is fitted to the outer circumferential surface of the tube 9, thereby positioning the tube 9 coaxially with the central axis 101. Accordingly, in the vicinity of the boundary between the tube 9 and the step surface 27, the inner circumferential surface of the tube 9 and the inner circumferential surface of the flow channel 22 of the second member 20 are smoothly continuous with each other without a gap in the direction of the central axis 101 and without misalignment (or a level difference) in the radial direction.

The connector 1 can be repeatedly connected to and disconnected from a female connector that includes a female member into which the male member 51 can be inserted. The female connector can have any suitable configuration. For example, the female member may have an inner circumferential surface (female tapered surface) that fits to the outer circumferential surface (male tapered surface) 52 of the male member 51. The female connector may have, on an outer circumferential surface of the female member, a male thread onto which the female thread 54 can be screwed. The connector 1 may also be configured to be connectable to a second connector 2b (see FIG. 6) of Embodiment 2 and a second connector 3b (see FIG. 11) of Embodiment 3, which will be described later. In the present invention, a connector (female connector in the case of Embodiment 1) to which the connector (connector 1 in the case of Embodiment 1) of the present invention can be connected is referred to as a "counterpart connector". A portion (the male member 51 and the female thread 54 in the case of Embodiment 1) of the connector of the present invention that is involved in the connection to the counterpart connector are referred to as a "main portion". The main portion is provided in the first member 10.

The materials of the first member 10 and the second member 20 are not limited to specific materials, but a hard material is preferable. The material of the first member 10 and the material of the second member 20 may be the same, or may be different from each other. For example, the material of the first member 10 can be selected with consideration given to strength, durability, sealability, and the like that are required for connection to and disconnection from the counterpart connector (female connector). Specifically, resin materials such as polypropylene, polyethylene, polycarbonate, polyacetal, polyamide, hard polyvinyl chloride, styrene-ethylene, polyethylene terephthalate, polybutylene terephthalate, and a butylene-styrene block copolymer can be used as the material of the first member 10. On the other hand, the material of the second member 20 can be selected with consideration given to the connectivity to the tube 9. The method for connecting the second member 20 to the tube 9 is not limited, and a method commonly used in the art, for example, adhesion using a solvent or thermal fusing can be used. For example, in the case where the material of the tube 9 is soft polyvinyl chloride or polybutadiene, hard polyvinyl chloride or polybutadiene can be used as the material of the second member 20. These materials that are preferable for the second member 20 are relatively soft, compared with the aforementioned materials that are preferable for the first member 10. This is advantageous in forming a liquid-tight seal (details will be described later) between the first member 10 and the second member 20. With regard to each of the first member 10 and the second member 20, the entire member can be integrally produced as a single component through injection molding or the like using any of the aforementioned materials.

The connector 1 of Embodiment 1 includes the first member 10, which has the main portion (male member 51 and female thread 54) that can be repeatedly connected to and disconnected from the counterpart connector (female connector), and the second member 20, which can be connected to the tube 9. A material that has good connectivity to the tube 9 can be selected as the material of the second member 20. The first member 10 and the second member 20 are produced separately and then coupled to each other to form a single unit. The coupling between the first member 10 and the second member 20 can be achieved simply by pushing the inner cylindrical portion 40 of the second member 20 into the outer cylindrical portion 30 of the first member 10. When compared with the connector of Patent Document 2 described above, which is produced by integrating two members with each other using a two-color injection molding method, the connector 1 of the Embodiment 1 can be produced much more easily.

In order to connect the connector 1 to a plurality of types of tubes 9 made of different materials and having different dimensions (inner diameters and outer diameters), a plurality of types of second members 20 suited to the respective types of tubes can be prepared. A second member 20 suited to a given tube 9 is selected from the plurality of types of second members 20 and coupled to the first member 10. Thus, a common first member 10 can be used for a plurality of types of tubes 9.

Also, in order to connect the connector 1 to a plurality of types of female connectors that meet different specifications (standards), a plurality of types of first members 10 suited to the respective types of female connectors can be prepared. A first member 10 suited to a given female connector is selected from the plurality of types of first members 10 and coupled to the second member 20. Thus, a common second member 20 can be used for a plurality of types of female connectors.

As described above, with the connector 1 of Embodiment 1, multiple types of connectors can be obtained by replacing the first member 10 or the second member 20 with a first or second member that has a different configuration. Therefore, the connector 1 is highly versatile.

The tube 9 and the male member 51 are in communication with each other via the flow channel 102. The flow channel 102 is constituted by the flow channel 12 of the first member 10 and the flow channel 22 of the second member 20. As a result of the first engagement portions 31 and the second engagement portion 41 engaging each other, the leading end 45 of the inner cylindrical portion 40 abuts against the annular rib 35 of the outer cylindrical portion 30 along the central axis 101. Also, as a result of the first fitting surface 32 of the outer cylindrical portion 30 and the second fitting surface 42 of the inner cylindrical portion 40 being fitted to each other, the outer cylindrical portion 30 and the inner cylindrical portion 40 are coaxially positioned. Consequently, no gaps and no level differences are created between the flow channel 12 and the flow channel 22.

In general, if a flow channel is formed by coupling two components that have been separately produced to each other such that flow channels of the two components are in communication with each other, inner circumferential surfaces that define the respective flow channels are likely to create a gap and a level difference at a boundary portion between the two components. Such a gap and a level difference are highly likely to form a stagnation portion where a liquid flowing through the flow channel stagnates. The stagnation portion is likely to cause the following problems: in the case where the liquid is a drug solution, the ratio of a drug will change as a result of the drug stagnating in the stagnation portion for a long period of time; in the case where the liquid is blood, a blood clot will form in the stagnation portion; in the case where the liquid is contaminated with bacteria, the bacteria will grow in the stagnation portion; in the case where a bubble in the liquid stays in the stagnation portion, it will be difficult to remove the bubble; and so on. In Embodiment 1, despite the fact that the flow channel 102 of the connector 1 is constituted by the flow channel 12 of the first member 10 and the flow channel 22 of the second member 20, a stagnation portion is unlikely to be formed at a boundary portion between the flow channel 12 and the flow channel 22. Thus, the likelihood of the above-described problems occurring is low.

A liquid-tight seal is formed at least either between the first fitting surface 32 and the second fitting surface 42, or between the annular rib 35 and the leading end 45 of the inner cylindrical portion 40, or preferably both. This seal prevents the liquid that flows through the flow channel 102 from leaking out of the connector 1 through a gap between the first member 10 and the second member 20. Despite the fact that the flow channel 102 is constituted by the flow channel 12 of the first member 10 and the flow channel 22 of the second member 20, the likelihood of the liquid leaking is low. In general, a good seal can be easily formed by the first fitting surface 32 and the second fitting surface 42 being fitted to each other. The first fitting surface 32 and the second fitting surface 42 may be in surface contact with each other over a wide area in the direction of the central axis 101 (so-called taper fitting), or may be in contact with each other in a relatively narrow, limited region. Local contact is advantageous in improving the sealability. In the present embodiment, the boundary between the tapered surface 321 and the circular cylindrical surface 322 as well as a portion in the vicinity of the boundary are in local contact with a portion in the vicinity of the distal end of the second fitting surface 42.

In the connector 1 of Embodiment 1, in a state in which the first member 10 and the second member 20 are coupled to each other (i.e., in a state in which the first engagement portions 31 and the second engagement portion 41 have engaged each other), the first member 10 can rotate about the central axis 101 relative to the second member 20. This configuration has the following advantages. First, twisting in the tube 9 is prevented. For example, when the connector 1 is to be connected to or disconnected from a female connector, the female thread 54 needs to be screwed onto or unscrewed from a male thread of the female connector. At this time, it is possible to rotate only the first member 10, without rotating the second member 20. Therefore, the tube 9 connected to the second member 20 is prevented from becoming twisted. Secondly, the screw engagement between the female thread 54 and the male thread is prevented from coming loose due to the tube 9 twisting. For example, in a state in which the connector 1 is connected to the female connector, if the tube 9 connected to the second member 20 is twisted, a rotating force that is generated in the tube 9 to straighten the twist is transferred to the second member 20. The rotating force is not transferred to the first member 10 because the second member 20 rotates relative to the first member 10. Thus, the screw engagement between the female thread 54 and the male thread is prevented from coming loose.

In this manner, the coupling between the first member 10 and the second member 20 functions as a "revolute joint". In Embodiment 1, even when the first member 10 rotates relative to the second member 20, no gaps and no level differences are created between the flow channel 12 and the flow channel 22 as described above. Also, the liquid flowing through the flow channel 102 does not leak out of the connector 1 through a gap between the first member 10 and the second member 20. The first member 10 and the second member 20 are integrated with each other without looseness.

In order to facilitate rotation of the first member 10 relative to the second member 20, a lubricant may be added to a portion where the outer cylindrical portion 30 and the inner cylindrical portion 40 are in contact with each other, or, in particular, between the first fitting surface 32 and the second fitting surface 42. There is no limitation on the lubricant, and silicone oil can be used, for example. The lubricant is applied to the outer circumferential surface (in particular, the second fitting surface 42) of the inner cylindrical portion 40 before the inner cylindrical portion 40 is inserted into the outer cylindrical portion 30. The lubricant is also advantageous in improving the sealability between the first fitting surface 32 and the second fitting surface 42.

Note that, as is the case with a second connector 2b of Embodiment 2 and a first connector 3a and a second connector 3b of Embodiment 3, which will be described later, the connector 1 may also be configured such that the first member 10 is unrotatable relative to the second member 20.

The first member 10 includes, on its distal side (the opposite side to the coupling portion 100), a main portion that can be repeatedly connected to and disconnected from an additional connector (counterpart connector) other than the connector 1. In Embodiment 1, the main portion includes the male member 51 and the female thread 54 so as to be connectable to the second connector 2b (see FIG. 6) of Embodiment 2 and the second connector 3b (see FIG. 11) of Embodiment 3, which will be described later. However, the configuration of the main portion is not limited to this configuration, and a suitable modification can be made thereto depending on the counterpart connector. For example, the main portion can be configured such that the connector 1 is connectable to a bypass injection port 90 (see FIGS. 6 and 11) of Embodiment 2 or 3, which will be described later. In this case, instead of the female thread 54, two grooves (or protrusions) engageable with two claws (protrusions) 93 that protrude from an outer circumferential surface of the bypass injection port 90 may be provided as a lock mechanism for maintaining a state in which the connector 1 is connected to the bypass injection port 90 (see Patent Document 3, for example). The lock mechanism for maintaining a state in which the connector 1 is connected to the counterpart connector may also be realized by, instead of the lock cylinder 53 and the female thread 54, a swingable lock lever provided with a claw that is engageable with the counterpart connector. A configuration may also be adopted in which the main portion does not include a lock mechanism (the lock cylinder 53 and the female thread 54). The male member 51 that constitutes the main portion may be a puncture needle having a sharp tip with which a rubber stopper or the like can be pierced. The connector 1 may also be a female connector instead of a male connector. In this case, the main portion of the first member 10 may include, for example, a female member 61 provided with a male thread 64 of Embodiments 2 and 3 (see FIGS. 6, 10, and 11), which will be described later, instead of the male member 51, the lock cylinder 53, and the female thread 54.

Embodiment 2

Figure 6:
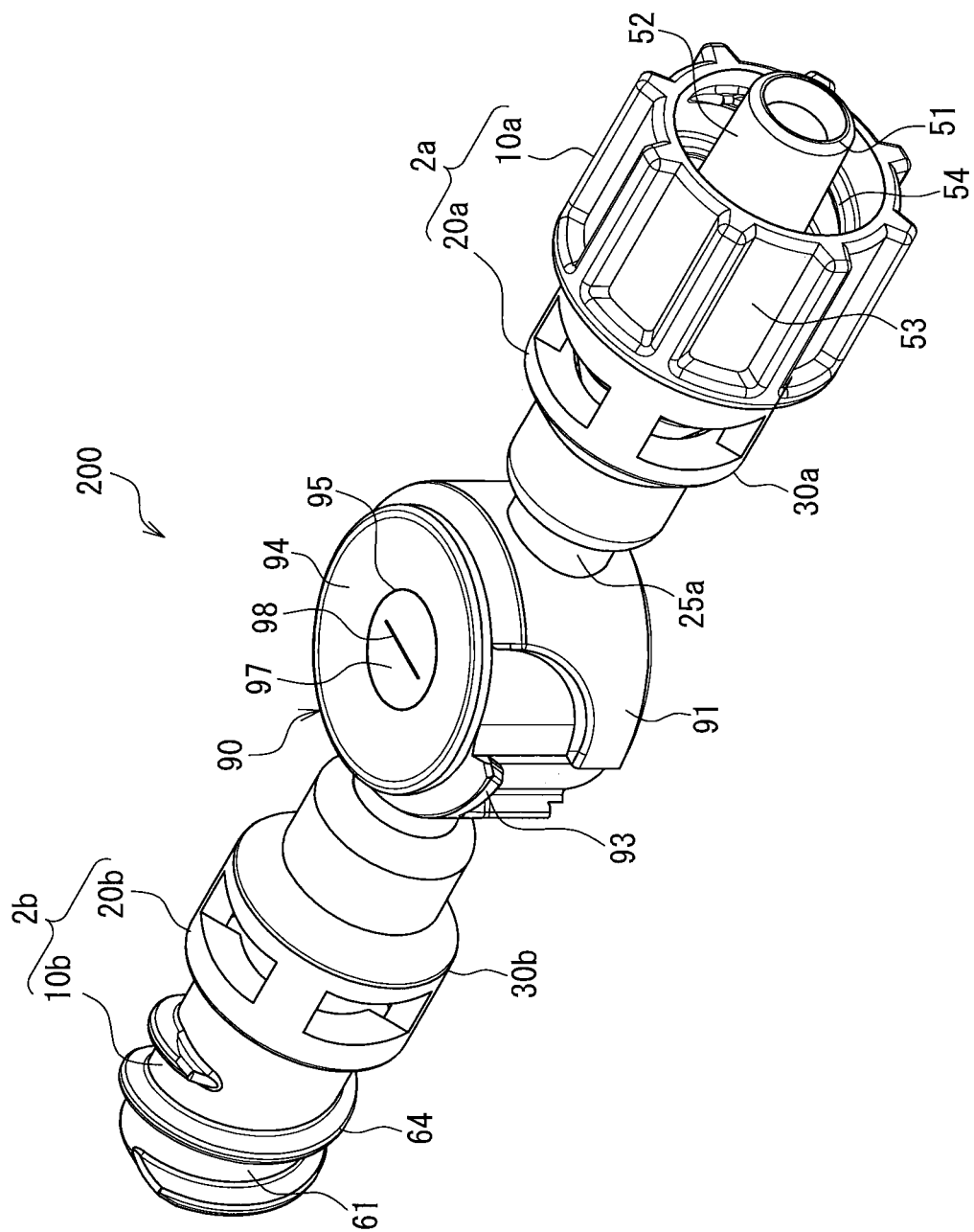
FIG. 6 is a perspective view of a bypass injection port assembly including a first connector and a second connector according to Embodiment 2 of the present invention.
Figure 7:
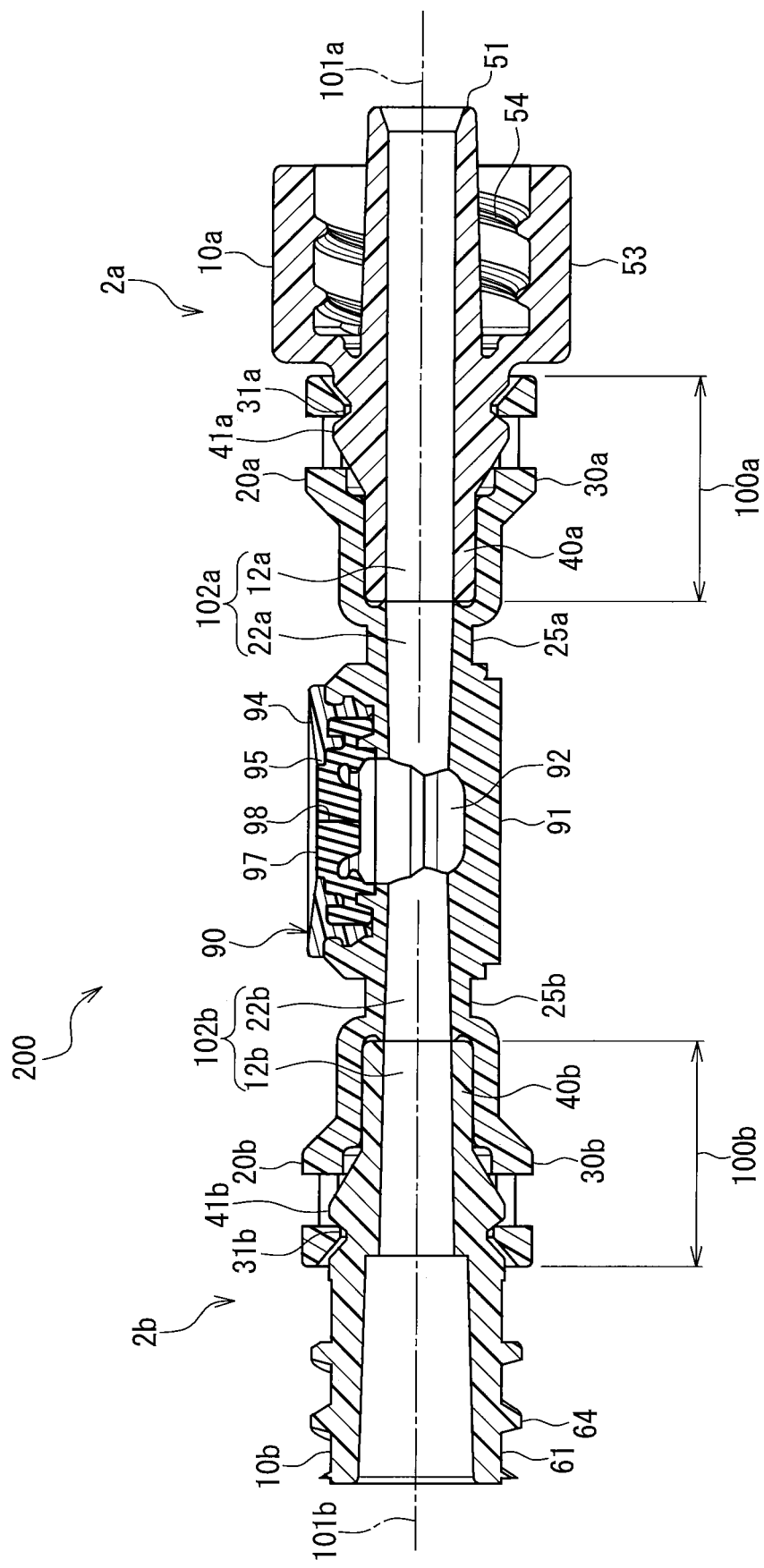
FIG. 7 is a cross-sectional view of the bypass injection port assembly including the first and the second connectors according to Embodiment 2 of the present invention.
Figure 8:
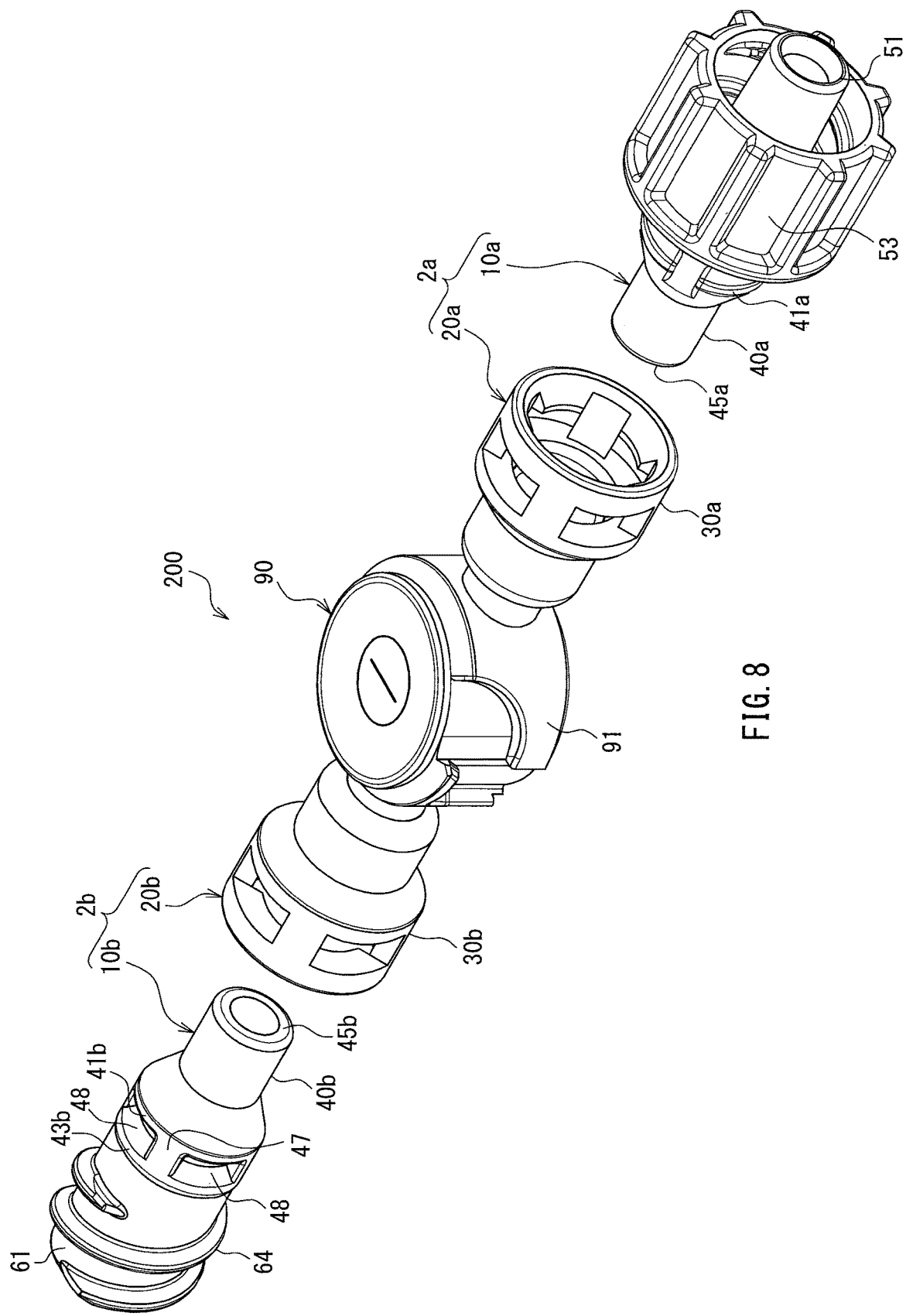
FIG. 8 is an exploded perspective view of the bypass injection port assembly including the first and the second connectors according to Embodiment 2 of the present invention.

FIG. 6 is a perspective view of a bypass injection port assembly 200 according to Embodiment 2 of the present invention. FIG. 7 is a cross-sectional view of the bypass injection port assembly 200, and FIG. 8 is an exploded perspective view of the bypass injection port assembly 200. The bypass injection port assembly 200 includes a bypass injection port (also referred to as "coinfusion port") 90, as well as a first connector 2a and a second connector 2b that are arranged on opposite sides of the bypass injection port 90.

The bypass injection port 90 includes a base portion 91, a cap 94, and a septum (partition wall member) 97. The base portion 91 has a bottomed, substantially circular cylindrical shape that is open upward. Two claws (protrusions) 93 (only one of the claws 93 can be seen in FIGS. 6 and 8) for maintaining a state in which a male connector (not shown) that can be connected to the bypass injection port 90 is connected are provided on an outer circumferential surface of the base portion 91. The septum 97 is placed so as to close the upper opening of the base portion 91. The cap 94 is mounted to the base portion 91 so as to cover the septum 97. A central portion of the septum (partition wall member) 97 is exposed from an opening 95 in an upper surface of the cap 94. The septum 97 is a thin circular plate made of a soft material (a so-called elastomer) that has rubber elasticity (or flexibility), such as rubber or a thermoplastic elastomer. A straight-line shaped slit (cut) 98 penetrating the septum 97 in its thickness direction is formed at the center of the septum 97. In an initial state in which the septum 97 is not deformed, the slit 98 is closed and forms a liquid-tight seal. When a cylindrical male member (male luer, not shown) that does not have a sharp tip is inserted into the slit 98 of the septum 97, the septum 97 elastically deforms, and an inner cavity 92 of the base portion 91 and the male member thus come into communication with each other. When the male member is withdrawn from the septum 97, the septum 97 immediately returns to the initial state, and the slit 98 is closed liquid-tight. In this manner, the septum 97 functions as a self-closing valve. The bypass injection port 90 is a female connector that has such resealability, and is known from Patent Documents 3 to 5, for example.

The first connector 2a, the second connector 2b, and the bypass injection port 90 located therebetween are arranged in a straight line. The first connector 2a includes a first member 10a that has a male member 51, and a second member 20a that is provided integrally with an outer circumferential wall of the base portion 91. The first member 10a is inserted into the second member 20a, and the two members are thus coupled to each other. The second connector 2b includes a first member 10b that has a female member 61, and a second member 20b that is provided integrally with the outer circumferential wall of the base portion 91. The first member 10b is inserted into the second member 20b, and the two members are thus coupled to each other. The first and the second connectors 2a and 2b are the connectors of the present invention.

For the sake of convenience of the following description, relative to the bypass injection port 90, a side that is close to the bypass injection port 90 will be referred to as a "proximal" side, and a side that is far from the bypass injection port 90 will be referred to as a "distal" side. In the drawings that will be taken into account in the following description, among the constituent members of the first and the second connectors 2a and 2b, members that correspond to the constituent members of the connector 1 of Embodiment 1 are denoted by the same reference numerals as those assigned to the members of Embodiment 1. Note that, for members that belong to both the first connector 2a and the second connector 2b, in order to distinguish between the members that belong to the first connector 2a and the members that belong to the second connector 2b, the reference numerals of the members that belong to the first connector 2a are given a suffix "a", and the reference numerals of the members that belong to the second connector 2b are given a suffix "b". The reference numerals of members that belong to only one of the first connector 2a and the second connector 2b are not given the suffixes "a" and "b". For example, a member denoted by a reference numeral "30a" is an "outer cylindrical portion" corresponding to the "outer cylindrical portion 30" of Embodiment 1 and belongs to the first connector 2a. For members that correspond to the members described in Embodiment 1, redundant descriptions are omitted. Hereinafter, Embodiment 2 will be described focusing on the differences from Embodiment 1.

Unlike the connector 1 of Embodiment 1, in the connectors 2a and 2b of Embodiment 2, the first members 10a and 10b include inner cylindrical portions 40a and 40b, and the second members 20a and 20b include outer cylindrical portions 30a and 30b. The inner cylindrical portions 40a and 40b are fitted into the outer cylindrical portions 30a and 30b, respectively.

Figure 9:
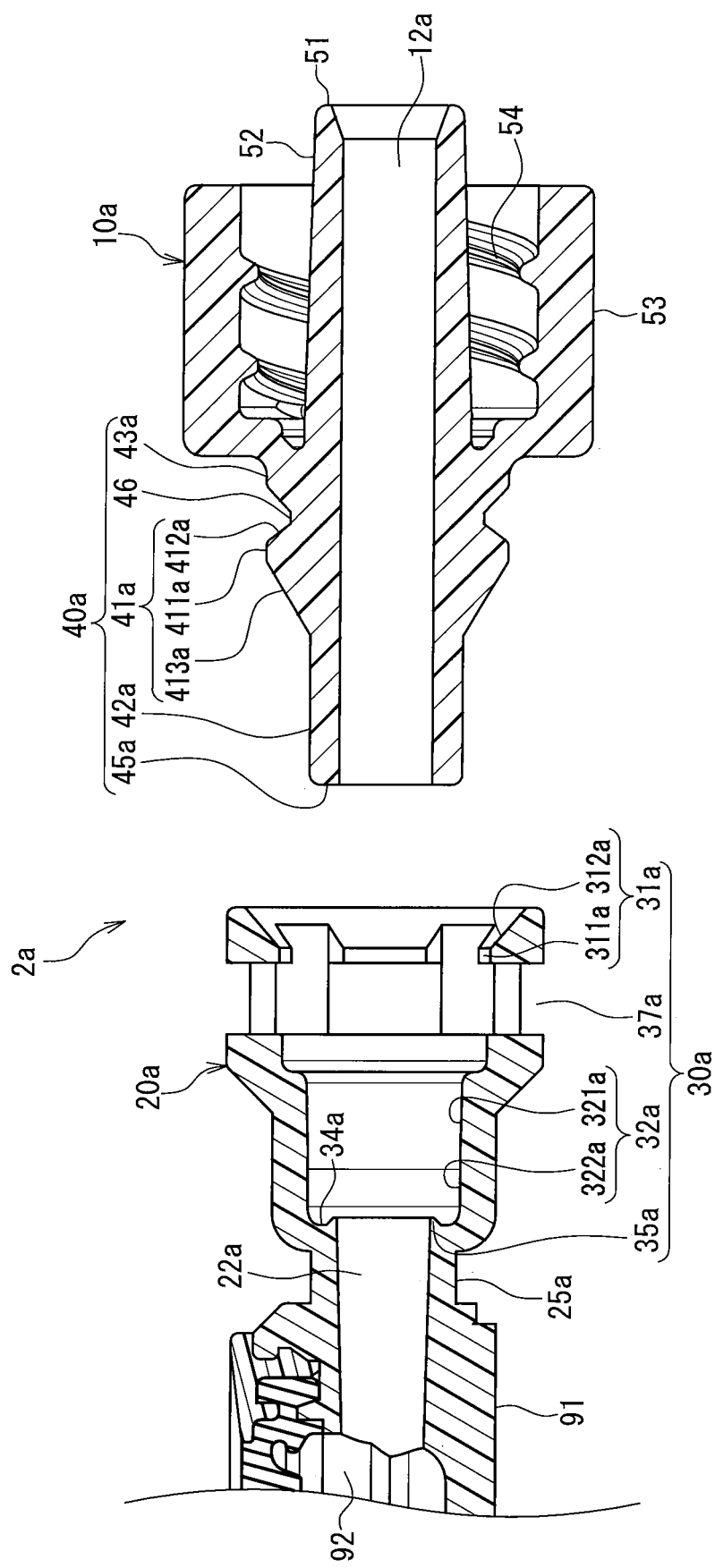
FIG. 9 is an exploded cross-sectional view of the first connector of Embodiment 2 of the present invention.

Now, the first connector 2a will be described. FIG. 9 is an exploded cross-sectional view of the first connector 2a.

The first member 10a includes, on the distal side, the male member 51 and a lock cylinder 53 on which a female thread 54 is provided, and also includes, on the proximal side, the inner cylindrical portion 40a. A flow channel 12a passes through the first member 10a from the distal end to the proximal end of the first member 10a, and the male member 51 and the inner cylindrical portion 40a are thus in communication with each other via the flow channel 12a. The male member 51 and the female thread 54 together constitute a so-called screw-lock type male connector (see Patent Document 1, for example).

The inner cylindrical portion 40a has, at its proximal end, a leading end 45a, and an outer circumferential surface of the inner cylindrical portion 40a has a second fitting surface 42a, a second engagement portion 41a, and a protrusion 43a that are sequentially provided in this order from the leading end 45a (proximal side) toward the male member 51 (distal side), as is the case with the inner cylindrical portion 40 (see FIGS. 4A and 4B) of Embodiment 1. A recess 46 is formed between the second engagement portion 41a and the protrusion 43a.

The second member 20a includes a base portion 25a on the proximal side and the outer cylindrical portion 30a on the distal side. Unlike the base portion 25 of Embodiment 1, a proximal end of the base portion 25a is connected to the base portion 91 of the bypass injection port 90. The base portion 25a has a hollow, substantially circular cylindrical shape. A flow channel 22a that is in communication with the inner cavity 92 of the bypass injection port 90 passes through the base portion 25a.

An inner circumferential surface of the outer cylindrical portion 30a has four first engagement portions 31a, a first fitting surface 32a, and an annular rib 35a that are sequentially provided in this order from an open end (distal end) of the outer cylindrical portion 30a toward the base portion 25a, as is the case with the outer cylindrical portion 30 (see FIGS. 3A and 3B) of Embodiment 1. The inner diameter of the flow channel 22a at its distal end (i.e., the annular rib 35a) is set to be equal to the inner diameter of the flow channel 12a of the first member 10a at its proximal end (i.e., the leading end 45a).

As shown in FIGS. 6 and 7, as in the case of Embodiment 1, the inner cylindrical portion 40a is inserted in the outer cylindrical portion 30a, and the first member 10a and the second member 20a are thus coupled to each other. In a coupling portion 100a, the outer cylindrical portion 30a and the inner cylindrical portion 40a together constitute a double-tube structure. The flow channel 12a of the first member 10a and the flow channel 22a of the second member 20a are in communication with each other, thereby forming a flow channel 102a of the first connector 2a. The bypass injection port 90 is in communication with the male member 51 via the flow channel 102a.

Figure 10:
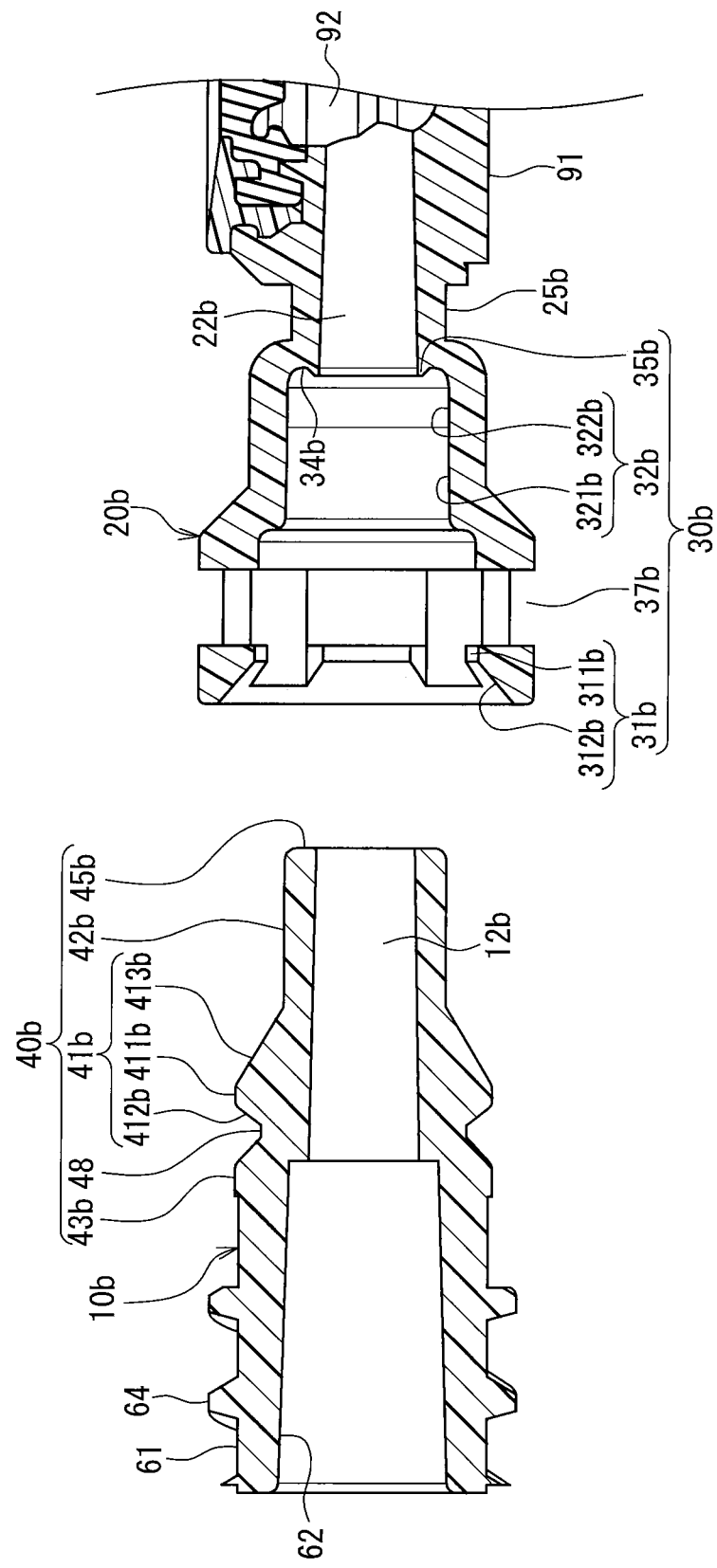
FIG. 10 is an exploded cross-sectional view of the second connector of Embodiment 2 of the present invention.

Now, the second connector 2b will be described. FIG. 10 is an exploded cross-sectional view of the second connector 2b.

The first member 10b includes the female member 61 on the distal side, and the inner cylindrical portion 40b on the proximal side. The female member 61 has a hollow cylindrical shape. An inner circumferential surface 62 of the female member 61 is a tapered surface (so-called female tapered surface) whose inner diameter gradually increases toward a distal end (end on the opposite side to the inner cylindrical portion 40b) of the female member 61. A male thread 64 is formed on an outer circumferential surface of the female member 61. The female member 61 provided with the male thread 64 constitutes a so-called screw-lock type female connector (see Patent Document 1, for example).

The inner cylindrical portion 40b has a hollow, substantially circular cylindrical shape through which a flow channel 12b passes. The inner cylindrical portion 40b has, at its proximal end, a leading end 45b, and an outer circumferential surface of the inner cylindrical portion 40b has a second fitting surface 42b, a second engagement portion 41b, and a protrusion 43b that are sequentially provided in this order from the leading end 45b (proximal side) toward the female member 61 (distal side), as is the case with the inner cylindrical portion 40 (see FIGS. 4A and 4B) of Embodiment 1. In Embodiment 1, the recess 46 that is continuous in the circumferential direction is formed between the second engagement portion 41 and the protrusion 43 (see FIG. 2). In contrast, in Embodiment 2, the recess 46 is divided by four ribs 47 that connect the second engagement portion 41b and the protrusion 43b to each other in the direction of the central axis, as shown in FIG. 8. Accordingly, four independent recesses 48 are provided between the second engagement portion 41b and the protrusion 43b and arranged at regular intervals in the circumferential direction.

Referring again to FIG. 10, the second member 20b includes a base portion 25b on the proximal side, and the outer cylindrical portion 30b on the distal side. A flow channel 22b that is in communication with the inner cavity 92 of the bypass injection port 90 passes through the base portion 25b. The second member 20b is symmetrical to the second member 20a (see FIG. 9) with respect to the bypass injection port 90.

As shown in FIGS. 6 and 7, as in the case of Embodiment 1, the inner cylindrical portion 40b is inserted in the outer cylindrical portion 30b, and the first member 10b and the second member 20b are thus coupled to each other. In a coupling portion 100b, the outer cylindrical portion 30b and the inner cylindrical portion 40b together constitute a double-tube structure. The flow channel 12b of the first member 10b and the flow channel 22b of the second member 20b are in communication with each other, thereby forming a flow channel 102b of the second connector 2b. The bypass injection port 90 is in communication with the female member 61 via the flow channel 102b.

As is the case with the connector 1 of Embodiment 1, the first connector 2a can be repeatedly connected to and disconnected from a female connector that includes a female member into which the male member 51 can be inserted. The female connector can have any suitable configuration. For example, the female member may have an inner circumferential surface (female tapered surface) that can fit to the outer circumferential surface (male tapered surface) 52 of the male member 51. The female connector may have, on an outer circumferential surface of the female member, a male thread onto which the female thread 54 can be screwed. The female connector may have a configuration similar to the female member 61 and the male thread 64 that are provided in the first member 10b of the second connector 2b. The female connector may be provided at an end of a flexible tube.

The second connector 2b can be repeatedly connected to and disconnected from a male connector that includes a male member that can be inserted into the female member 61. The male connector can have any suitable configuration. For example, the male member may have an outer circumferential surface (male tapered surface) that can fit to the inner circumferential surface (female tapered surface) 62 of the female member 61. The male connector may have a female thread into which the male thread 64 can be screwed. The second connector 2b may be configured so as to be connectable to the connector 1 of Embodiment 1 (see FIG. 1).

The first connector 2a and the second connector 2b may also be configured so as to be connectable to each other. In this case, a plurality of bypass injection port assemblies 200 can be connected in series.

The second member 20 (see FIG. 2) of Embodiment 1 is connected to the tube 9. For this purpose, the material of the second member 20 is selected with consideration given to the connectivity to the tube 9. In contrast, in the present embodiment, the second members 20a and 20b are produced integrally with the base portion 91 of the bypass injection port 90 to form a single component. There is no need to consider the connectivity to the tube 9 in selecting the materials of the second members 20a and 20b. There is no limitation on the materials of the second members 20a and 20b, and, for example, a resin material that was given as an example of the material of the first member 10 in Embodiment 1 can be used. There also is no limitation on the material of the cap 94, and, for example, a resin material that was given as an example of the first member 10 in Embodiment 1 can be used.

The connectors 2a and 2b of Embodiment 2 can be produced by pushing the first members 10a and 10b into the second members 20a and 20b, respectively, and thereby coupling the first members 10a and 10b to the second members 20a and 20b, respectively. Accordingly, like the connector 1 of Embodiment 1, the connectors 2a and 2b can be easily produced.

In order to connect the first connector 2a to a plurality of types of female connectors that meet different specifications (standards), a plurality of types of first members 10a suited to the respective types of female connectors can be prepared. Similarly, in order to connect the second connector 2b to a plurality of types of male connectors that meet different specifications (standards), a plurality of types of first members 10b suited to the respective types of male connectors can be prepared. The first members 10a and 10b can be replaced depending on respective counterpart connectors that are to be connected to the connectors 2a and 2b. The first connector 2a can be changed to a female connector by replacing the first member 10a with the first member 10b, which includes the female member 61. Also, the second connector 2b can be changed to a male connector by replacing the first member 10b with the first member 10a, which includes the male member 51. Thus, the connectors 2a and 2b are highly versatile.

In the second connector 2b, first engagement portions 31b of the outer cylindrical portion 30b are fitted into the recesses 48 (see FIG. 8) of the inner cylindrical portion 40b. The ribs 47 between the recesses 48 that are adjacent to each other in the circumferential direction abut against the first engagement portions 31b, and therefore, the first member 10b cannot rotate relative to the second member 20b. The first engagement portions 31b of the outer cylindrical portion 30b and the ribs 47 of the inner cylindrical portion 40b function as a "rotation preventing mechanism" that prevents rotation of the first member 10b relative to the second member 20b. When the second connector 2b is to be connected to or disconnected from a male connector (counterpart connector), the male thread 64 needs to be screwed onto or unscrewed from a female thread of the male connector. At this time, if the first member 10b on which the male thread 64 is provided rotates relative to the second member 20b (i.e., the bypass injection port 90), it may be difficult to screw or unscrew the male thread 64 onto or from the female thread. In Embodiment 2, the first member 10b is inhibited from rotating relative to the second member 20b (and furthermore, the bypass injection port 90), and therefore, the male connector and the second connector 2b can be easily connected to each other or disconnected from each other by, for example, holding the male connector (counterpart connector) and the bypass injection port 90 in different hands and rotating them in opposite directions.

Note that, in Embodiment 2, it is also possible to omit the ribs 47 and configure the first member 10b so as to be rotatable relative to the second member 20b. That is to say, the first member 10b may be replaced with a first member that is not provided with the ribs 47. In this case, the first members 10a and 10b are rotatable relative to the respective second members 20a and 20b (and furthermore, the bypass injection port 90). For example, in the case where the bypass injection port assembly 200 is provided in the middle of a liquid flow channel constituted by tubes, it is possible to rotate the bypass injection port 90 so that it is oriented in any desired direction without twisting the tubes.

Alternatively, in the first connector 2a, a configuration may be adopted in which the recess 46 between the second engagement portion 41a and the protrusion 43a is divided by ribs 47 so that, as is the case with the second connector 2b, the first member 10a is made unrotatable relative to the second member 20a.

The base portion 91 of the bypass injection port 90, the second member 20a, and the second member 20b may be produced separately and then coupled to each other to form a single component. In this case, multiple types of bypass injection port assemblies 200 can be obtained by replacing one or two of the base portion 91 and the second members 20a and 20b with another, or others, having a different configuration(s).

As is the case with the first member 10 of Embodiment 1, various modifications can be made to the main portion of the first member 10a. Also, the main portion of the first member 10b is not limited to the present embodiment as well, and a suitable modification can be made thereto. For example, the first member 10b may not include the male thread 64.

Embodiment 2 is the same as the Embodiment 1 except for the above-described differences. The description of Embodiment 1 is also applicable to Embodiment 2 as appropriate.

Embodiment 3

Figure 11:
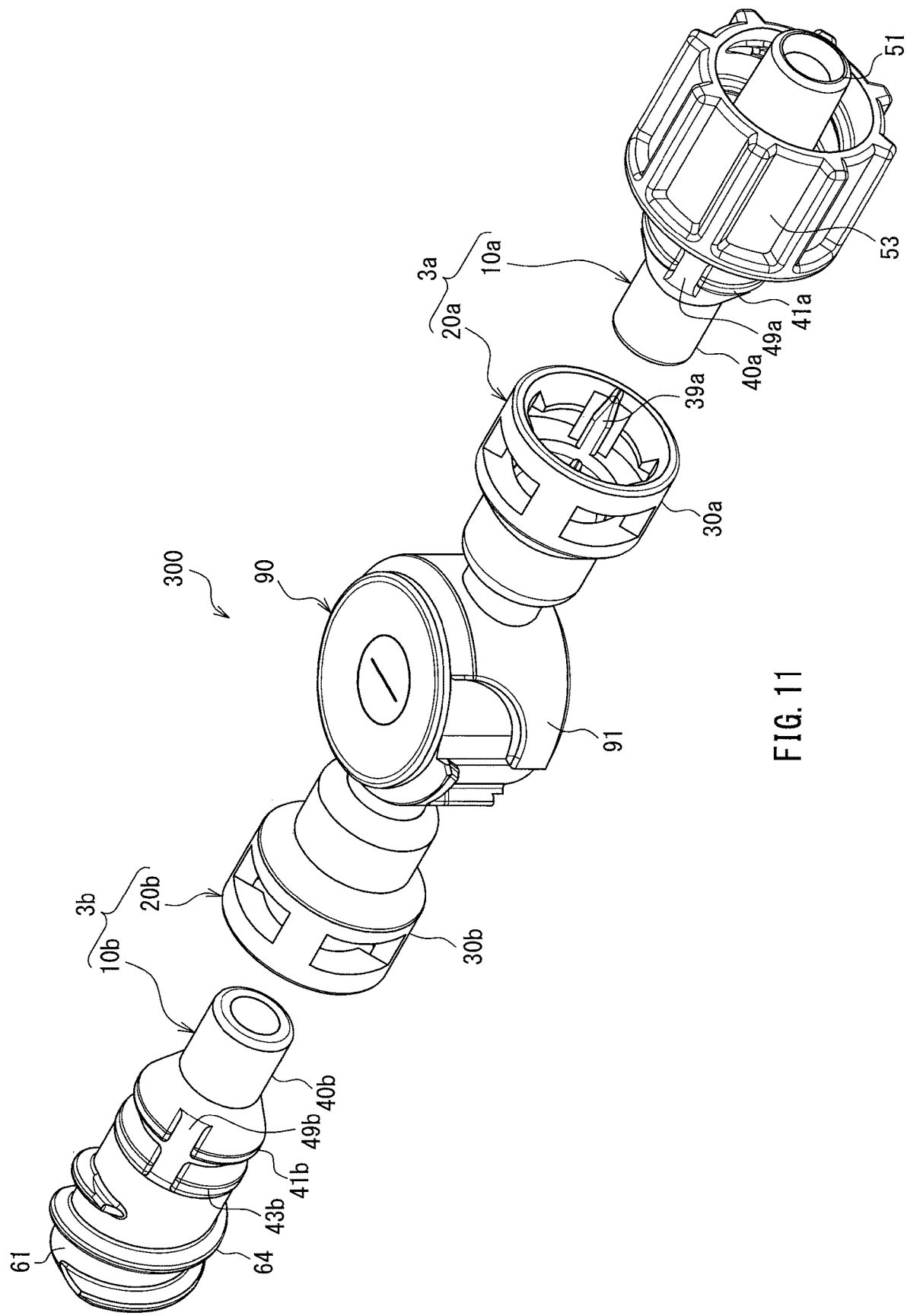
FIG. 11 is an exploded perspective view of a bypass injection port assembly including a first connector and a second connector according to Embodiment 3 of the present invention.
Figure 12:
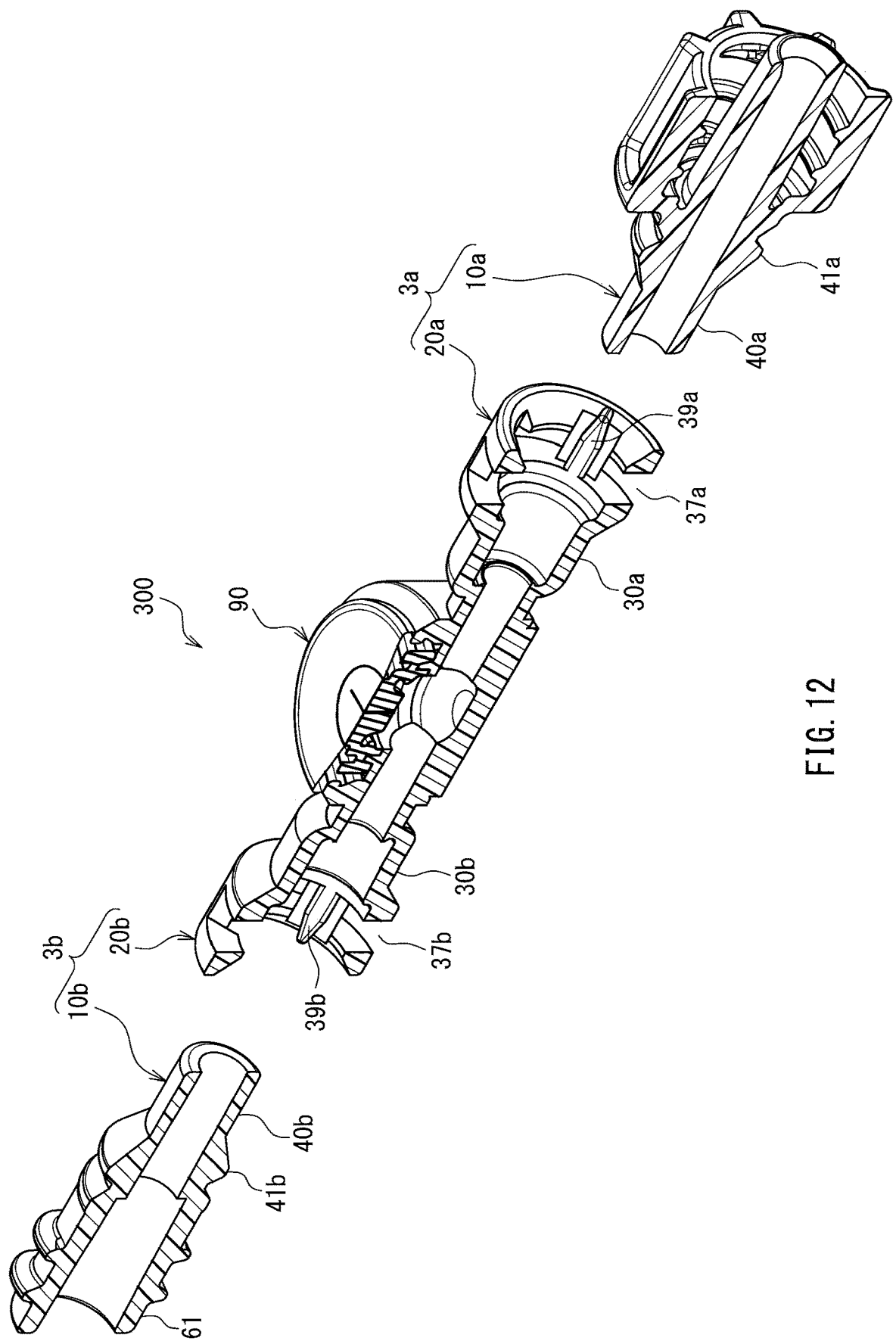
FIG. 12 is an exploded cross-sectional perspective view of the bypass injection port assembly including the first and the second connectors according to Embodiment 3 of the present invention.

FIG. 11 is an exploded perspective view of a bypass injection port assembly 300 according to Embodiment 3 of the present invention. FIG. 12 is an exploded cross-sectional perspective view of the bypass injection port assembly 300. As is the case with the bypass injection port assembly 200 of Embodiment 2, the bypass injection port assembly 300 includes a bypass injection port 90, as well as a first connector 3a and a second connector 3b that are arranged on opposite sides of the bypass injection port 90. The first and the second connectors 3a and 3b are the connectors of the present invention. The appearance of the bypass injection port assembly 300 is the same as that of the bypass injection port assembly 200 (see FIG. 6) of Embodiment 2, and therefore, drawings thereof are omitted.

The differences of the bypass injection port assembly 300 from the bypass injection port assembly 200 are as follows. First, in the bypass injection port assembly 300, both of the first and the second connectors 3a and 3b are configured such that the first members 10a and 10b are unrotatable relative to the second members 20a and 20b. Second, Embodiment 3 differs from Embodiment 2 in terms of a mechanism (rotation preventing mechanism) for making the first members 10a and 10b unrotatable relative to the second members 20a and 20b. Hereinafter, Embodiment 3 will be described focusing on the differences from Embodiment 2.

As shown in FIG. 11, in Embodiment 3, the ribs 47 (see FIG. 8) of Embodiment 2 are not provided on the outer circumferential surfaces of the inner cylindrical portions 40a and 40b. Instead, grooves 49a and 49b are provided in the outer circumferential surfaces of the inner cylindrical portions 40a and 40b. That is to say, two linear grooves 49a extending in the direction of the central axis are provided in the outer circumferential surface of the inner cylindrical portion 40a such that the grooves 49a divide the second engagement portion 41a into two equal parts in the circumferential direction (only one of the grooves 49a can be seen in FIG. 11). Similarly, two linear grooves 49b extending in the direction of the central axis are provided in the outer circumferential surface of the inner cylindrical portion 40b such that the grooves 49b divide the second engagement portion 41b into two equal parts in the circumferential direction (only one of the grooves 49b can be seen in FIG. 11). In FIG. 11, a portion of the groove 49a on the distal side cannot be seen, but the groove 49a extends in the same manner as the groove 49b.

On the other hand, ribs 39a and 39b are provided on inner circumferential surfaces of the outer cylindrical portions 30a and 30b and protrude inward in the radial direction therefrom. That is to say, as shown in FIG. 12, two linear ribs 39a (only one of the ribs 39a can be seen in FIG. 12) extending in the direction of the central axis are provided on the inner circumferential surface of the outer cylindrical portion 30a, at positions between lateral holes 37a that are adjacent to each other in the circumferential direction. Similarly, two linear ribs 39b (only one of the ribs 39b can be seen in FIG. 12) extending in the direction of the central axis are provided on the inner circumferential surface of the outer cylindrical portion 30b, at positions between lateral holes 37b that are adjacent to each other in the circumferential direction.

When the first members 10a and 10b are coupled to the second members 20a and 20b, respectively, the ribs 39a and 39b are fitted into the respective grooves 49a and 49b. The first members 10a and 10b cannot rotate relative to the respective second members 20a and 20b (and furthermore, the bypass injection port 90) because the ribs 39a and 39b abut against the second engagement portions 41a and 41b in the circumferential direction. According to Embodiment 3, it is easy to connect, for example, two bypass injection port assemblies 300 in series by connecting the first connector 3a and the second connector 3b to each other, and to disconnect the two bypass injection port assemblies 300 that are connected in series from each other. The reason for this is that the two bypass injection port assemblies 300 can be connected to and disconnected from each other simply by holding the bypass injection port 90 of one of the bypass injection port assemblies 300 and the bypass injection port 90 of the other bypass injection port assembly 300 in different hands and rotating them in opposite directions.

In Embodiment 3, the first connector 3a and the second connector 3b respectively do not need to have two sets of grooves (49a or 49b) and ribs (39a or 39b) that are fitted to each other, and may have one set, or three or more sets.

Either the ribs 39a, the ribs 39b, or both may be omitted. With this configuration, either the rotation of the first member 10a relative to the second member 20a, the rotation of the first member 10b relative to the second member 20b, or both can be made possible without changing the first members 10a and 10b.

Embodiment 3 is the same as Embodiments 1 and 2 except for the above-described differences. The description of Embodiments 1 and 2 is also applicable to Embodiment 3 as appropriate.

It should be understood that Embodiments 1 to 3 above are given by way of example only. The present invention is not limited to Embodiments 1 to 3, and a modification can be made thereto as appropriate.

In Embodiments 1 to 3 above, the annular rib 35 that functions as an abutment portion against which the leading end 45 of the inner cylindrical portion can abut is provided on the step surface 34 of the outer cylindrical portion. The annular rib 35 narrows a region against which the leading end 45 can abut, and is therefore advantageous in forming a liquid-tight seal between the leading end 45 and the annular rib 35. However, in the present invention, the annular rib 35 may be omitted. In other words, the leading end 45 may directly abut against the step surface 34. In this case, the step surface 34 functions as the abutment portion. Alternatively, an annular rib similar to the annular rib 35 may be provided on the leading end 45 of the inner cylindrical portion.

In order to enable the leading end 45 of the inner cylindrical portion to abut against the abutment portion (annular rib 35) of the outer cylindrical portion along the central axis, in Embodiments 1 to 3 above, the first inclined surface 412 against which the first engagement portions 31 of the outer cylindrical portion can abut is provided in the second engagement portion 41 of the inner cylindrical portion. However, in the present invention, a configuration other than this configuration may also be adopted to enable the leading end 45 of the inner cylindrical portion to abut against the abutment portion (annular rib 35) of the outer cylindrical portion. For example, a configuration may be adopted in which inclined surfaces are provided in the first engagement portions 31 of the outer cylindrical portion, the inclined surfaces being inclined such that the inner diameter of the outer cylindrical portion gradually increases from the crest portions 311 toward the abutment portion (annular rib 35) side, and the second engagement portion 41 abuts against these inclined surfaces.

In Embodiments 1 to 3 above, the four first engagement portions 31 are provided in the outer cylindrical portion. However, the number of first engagement portions 31 is not limited to four, and may also be less than four, or more than four. Moreover, a first engagement portion 31 that is continuous in the circumferential direction and has an annular shape may be provided.

In Embodiments 1 to 3 above, the second engagement portion 41 provided on the inner cylindrical portion is continuous in the circumferential direction. However, the second engagement portion 41 is not limited to this configuration. For example, the second engagement portion 41 may be divided in the circumferential direction at one or more locations.

In Embodiments 1 to 3 above, the protrusion 43 provided on the inner cylindrical portion is continuous in the circumferential direction. However, the protrusion 43 is not limited to this configuration. For example, the protrusion 43 may be divided in the circumferential direction at one or more locations. Alternatively, the protrusion 43 may be omitted.

The configuration of the rotation preventing mechanism for making the first member unrotatable relative to the second member is not limited to those described in Embodiments 2 and 3. In general, a rotation preventing mechanism can be constituted by engagement structures that are provided in the first member and the second member, respectively, and are engageable with each other. Any suitable combinations of engagement structures, such as a protrusion and a protrusion, or a protrusion and a recess, can be used as the engagement structures that are engageable with each other. The position at which the rotation preventing mechanism is provided is not limited to the positions described in Embodiments 2 and 3 above, and a suitable modification can be made thereto. The rotation preventing mechanism may also include an additional member in addition to the first and the second members.

The connector of the present invention constituted by the first and the second members is provided on an end of the tube 9 in Embodiment 1, or provided on the bypass injection port 90 in Embodiments 2 and 3. However, the connector of the present invention can be provided on any member other than these members. For example, the connector of the present invention can be provided on a cylindrical front end of a syringe, three ports of a three-way stopcock, a port of a pump for making a liquid flow, and the like.

In Embodiment 1, a configuration may also be adopted in which the first member 10 includes the inner cylindrical portion 40, and the second member 20 includes the outer cylindrical portion 30. In Embodiments 2 and 3, a configuration may also be adopted in which the first members 10a and 10b include the outer cylindrical portions 30a and 30b, and the second members 20a and 20b include the inner cylindrical portions 40a and 40b. When first members provided with the main portion are standardized to always include one of the outer cylindrical portion and the inner cylindrical portion, a first member can be adapted to any second member, such as a second member that is provided on the tube 9 or a second member that is provided on the bypass injection port 90. The versatility of the connector is thus enhanced even more.

The first member that constitutes the connector of the present invention includes, on the opposite side to the coupling portion, the main portion that can be repeatedly connected to and disconnected from a connector (counterpart connector) other than the connector of the present invention. The configuration of the main portion is not limited to those of Embodiments 1 to 3 above, and a suitable modification can be made thereto. In general, in the case where the counterpart connector is a female connector, the main portion includes a male member that can be inserted into a female member of the female connector, and in the case where the counterpart connector is a male connector, the main portion includes a female member into which a male member of the male connector can be inserted. The main portion may also include a self-closing type septum similar to the septum 97 of the bypass injection port 90. In this case, a coinfusion port (see Patent Document 6) can be configured using the connector of the present invention. The main portion may further include a lock mechanism for maintaining a state in which the connector is connected to the counterpart connector. A screw lock mechanism that uses fastening with a screw, a claw lock mechanism that uses engagement by means of a claw (protrusion), a lever lock mechanism that uses a swingable lever provided with a claw, and the like are examples of known lock mechanisms, and any of such lock mechanisms can be applied to the present invention.

INDUSTRIAL APPLICABILITY

While there is no limitation on the field of use of the present invention, the present invention can be widely used as a connector for forming a flow channel through which a liquid flows. The present invention can be particularly favorably used in the field of medicine. However, the present invention can also be used in any fields in which liquids are handled other than the field of medicine, such as the fields of food, chemistry, and the like.

LIST OF REFERENCE NUMERALS 1, 2a, 2b, 3a, 3b Connector
9 Tube
10, 10a, 10b First member
20, 20a, 20b Second member
30, 30a, 30b Outer cylindrical portion
31, 31a, 31b First engagement portion
32, 32a, 32b First fitting surface
35, 35a, 35b Annular rib (Abutment portion)
39a, 39b Rib
40, 40a, 40b Inner cylindrical portion
41, 41a, 41b Second engagement portion
412, 412a, 412b First inclined surface (Inclined surface)
42, 42a, 42b Second fitting surface
45, 45a, 45b Leading end of inner cylindrical portion
47 Rib
49a, 49b Groove
51 Male member (Main portion)
61 Female member (Main portion)
90 Bypass injection port
100, 100a, 100b Coupling portion
101, 101a, 101b Central axis of connector
102, 102a, 120b Flow channel of connector

The invention claimed is:

1. A connector comprising a first member and a second member, the first member and the second member being coupled to each other in a coupling portion,
wherein the first member includes, on a side opposite to the coupling portion, a main portion that can be connected to and disconnected from a counterpart connector other than the connector, a flow channel via which the main portion and the second member are in communication with each other extends along a central axis of the connector, one of the first member and the second member includes an outer cylindrical portion that has a hollow cylindrical shape and is coaxial with the central axis, the other of the first member and the second member includes an inner cylindrical portion that has a hollow cylindrical shape and is coaxial with the central axis, in the coupling portion, the inner cylindrical portion is fitted in the outer cylindrical portion, the outer cylindrical portion includes a first engagement portion and an abutment portion, the inner cylindrical portion includes a second engagement portion that engages the first engagement portion, and a leading end that is a front end of the inner cylindrical portion in a direction in which the inner cylindrical portion is fitted into the outer cylindrical portion, as a result of the first engagement portion and the second engagement portion engaging each other, the leading end of the inner cylindrical portion abuts against the abutment portion of the outer cylindrical portion along the central axis, and the abutment portion is an annular rib having a substantially circular cylindrical shape and protruding in such a manner that an inner circumferential surface of the flow channel of the one of the first member and the second member is extended toward the inner cylindrical portion.

2. The connector according to claim 1, wherein at least one of the first engagement portion and the second engagement portion has an inclined surface that is inclined relative to the central axis, and the inclined surface is inclined such that the leading end of the inner cylindrical portion abuts against the abutment portion of the outer cylindrical portion along the central axis.

3. The connector according to claim 1, wherein the leading end of the inner cylindrical portion annularly abuts against the abutment portion so as to surround the flow channel.

4. The connector according to claim 1, wherein an inner circumferential surface of the outer cylindrical portion has a first fitting surface, and an outer circumferential surface of the inner cylindrical portion has a second fitting surface that is fitted to the first fitting surface.

5. The connector according to claim 4, wherein, as a result of the first fitting surface and the second fitting surface being fitted to each other, the outer cylindrical portion and the inner cylindrical portion are coaxially positioned.

6. The connector according to claim 4, wherein a liquid-tight seal is formed between the first fitting surface and the second fitting surface.

7. The connector according to claim 4, wherein a lubricant is added between the first fitting surface and the second fitting surface.

8. The connector according to claim 1, wherein an inner circumferential surface of the flow channel is continuous without a level difference and a gap between the first member and the second member.

9. The connector according to claim 1, wherein the first member is rotatable relative to the second member.

10. The connector according to claim 1, wherein the first member is unrotatable relative to the second member.

11. The connector according to claim 1, wherein the main portion includes a male member or a female member.

12. The connector according to claim 1, wherein the second member is connectable to an end of a flexible tube.

13. The connector according to claim 1, wherein the second member is provided on a bypass injection port.

14. The connector according to claim 1, wherein the first member and the second member are made of different materials.

* * * * *